United States Patent
Tarcic et al.

(10) Patent No.: US 9,161,935 B2
(45) Date of Patent: Oct. 20, 2015

(54) USE OF LAQUINIMOD FOR TREATING CROHN'S DISEASE PATIENTS WHO FAILED FIRST-LINE ANTI-TNF THERAPY

(71) Applicants: Nora Tarcic, Modiin (IL); Asi Haviv, Kvutsat Shiller (IL); Eran Blaugrund, Rehovot (IL); Joel Kaye, Netanya (IL)

(72) Inventors: Nora Tarcic, Modiin (IL); Asi Haviv, Kvutsat Shiller (IL); Eran Blaugrund, Rehovot (IL); Joel Kaye, Netanya (IL)

(73) Assignee: TEVA PHARMACEUTICAL INDUSTRIES, LTD., Petach-Tikva (IL)

(*) Notice: Subject to any disclaimer, the term of this patent is extended or adjusted under 35 U.S.C. 154(b) by 117 days.

(21) Appl. No.: 13/757,004

(22) Filed: Feb. 1, 2013

(65) Prior Publication Data

US 2013/0203807 A1   Aug. 8, 2013

Related U.S. Application Data

(60) Provisional application No. 61/595,006, filed on Feb. 3, 2012.

(51) Int. Cl.
- *A61K 31/47* (2006.01)
- *A61K 9/48* (2006.01)
- *A61K 31/4704* (2006.01)

(52) U.S. Cl.
CPC .................................. *A61K 31/4704* (2013.01)

(58) Field of Classification Search
None
See application file for complete search history.

(56) References Cited

U.S. PATENT DOCUMENTS

| | | | |
|---|---|---|---|
| 3,024,257 A | 3/1962 | Millar et al. |
| 4,107,310 A | 8/1978 | Allais et al. |
| 4,547,511 A | 10/1985 | Eriksoo et al. |
| 4,628,053 A | 12/1986 | Fries et al. |
| 4,738,971 A | 4/1988 | Eriksoo et al. |
| 4,782,155 A | 11/1988 | Nakagawa et al. |
| 5,139,878 A | 8/1992 | Kim et al. |
| 5,716,638 A | 2/1998 | Touitou |
| 5,912,349 A | 6/1999 | Sih |
| 6,077,851 A | 6/2000 | Bjork et al. |
| 6,121,287 A | 9/2000 | Bjork et al. |
| 6,133,285 A | 10/2000 | Bjork et al. |
| 6,307,050 B1 | 10/2001 | Kwiatkowski et al. |
| 6,395,750 B1 | 5/2002 | Hedlund et al. |
| 6,593,343 B2 | 7/2003 | Björk et al. |
| 6,605,616 B1 | 8/2003 | Björk et al. |
| 6,696,407 B1 | 2/2004 | Longo et al. |
| 6,802,422 B2 | 10/2004 | Ots et al. |
| 6,875,869 B2 | 4/2005 | Jansson |
| 7,485,311 B2 | 2/2009 | Lue et al. |
| 7,560,100 B2 | 7/2009 | Pinchasi et al. |
| 7,560,557 B2 | 7/2009 | Jansson |
| 7,589,208 B2 | 9/2009 | Jansson et al. |
| 7,884,208 B2 | 2/2011 | Frenkel et al. |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,314,124 B2 | 11/2012 | Jansson et al. |
| 2002/0173520 A1 | 11/2002 | Bjork et al. |
| 2003/0087929 A1 | 5/2003 | Kimura et al. |
| 2003/0119826 A1 | 6/2003 | Manning et al. |
| 2003/0124187 A1 | 7/2003 | Mention et al. |
| 2004/0247673 A1 | 12/2004 | Fergione et al. |
| 2005/0074451 A1 | 4/2005 | Yednock et al. |
| 2005/0192315 A1 | 9/2005 | Jansson et al. |
| 2005/0215586 A1 | 9/2005 | Jansson et al. |
| 2005/0234238 A1 | 10/2005 | Dube et al. |
| 2005/0271717 A1 | 12/2005 | Berchielli et al. |
| 2006/0004019 A1 | 1/2006 | Lieberburg |
| 2006/0183105 A1 | 8/2006 | Aiyar et al. |
| 2006/0276393 A1 | 12/2006 | Milburn et al. |
| 2007/0086979 A1 | 4/2007 | Chevrier et al. |
| 2007/0207141 A1 | 9/2007 | Lieberburg |
| 2007/0218062 A1 | 9/2007 | Irving |
| 2007/0231319 A1 | 10/2007 | Yednock |
| 2007/0280891 A1 | 12/2007 | Tamarkin et al. |
| 2008/0044382 A1 | 2/2008 | Lieberburg |
| 2008/0063607 A1 | 3/2008 | Tamarkin et al. |
| 2008/0090897 A1 | 4/2008 | Steiner et al. |

(Continued)

FOREIGN PATENT DOCUMENTS

| | | |
|---|---|---|
| EP | 1073639 | 11/2002 |
| EP | 1097139 | 12/2002 |

(Continued)

OTHER PUBLICATIONS

Clinical Trial NCT00737932 2009.*
Ben-Horin et al. Aliment. Pharmacol. Ther. 2011 (33) 987-995.*
Yanai et al. The American Journal of Gastroenterology 2011 (106) 685-698.*
Written Opinion of the International Searching Authority issued Apr. 9, 2013 in connection with PCT International Application No. PCT/US13/24356.
PCT International Search Report issued Apr. 9, 2013 in connection with PCT International Application No. PCT/US13/24356.
Office Action issued by the U.S. Patent and Trademark Office on Sep. 20, 2012 in connection with U.S. Appl. No. 12/804,795.

(Continued)

*Primary Examiner* — Jeffrey S Lundgren
*Assistant Examiner* — Michael Schmitt
(74) *Attorney, Agent, or Firm* — John P. White; Gary J. Gershik; Cooper & Dunham LLP

(57) ABSTRACT

This application provides for a method of treating a human patient afflicted with anti-TNFα refractory Crohn's disease, of treating a human patient afflicted with non-fibrostenotic Crohn's disease, and of treating a human patient whose Crohn's disease had not been surgically treated, the method comprising periodically administering to the patient an amount of laquinimod or pharmaceutically acceptable salt thereof effective to treat the patient. This application also provides for a method of inducing or maintaining clinical remission in a human patient afflicted with Crohn's disease comprising periodically administering to the patient an amount of laquinimod effective to induce or maintain clinical remission in the patient, which amount of laquinimod is less than 0.5 mg/day.

21 Claims, 3 Drawing Sheets

(56) References Cited

U.S. PATENT DOCUMENTS

| | | | |
|---|---|---|---|
| 2008/0108641 | A1 | 5/2008 | Ajami et al. |
| 2008/0118553 | A1 | 5/2008 | Frenkel et al. |
| 2008/0166348 | A1 | 7/2008 | Kupper et al. |
| 2008/0206159 | A1 | 8/2008 | Tamarkin et al. |
| 2009/0048181 | A1 | 2/2009 | Schipper et al. |
| 2009/0062330 | A1 | 3/2009 | Kalafer et al. |
| 2009/0081259 | A1 | 3/2009 | Jonas et al. |
| 2009/0148462 | A1 | 6/2009 | Chevrier et al. |
| 2009/0156542 | A1 | 6/2009 | Purschke et al. |
| 2009/0221575 | A1 | 9/2009 | Gerber et al. |
| 2009/0258847 | A1 | 10/2009 | Schreiner et al. |
| 2010/0158903 | A1 | 6/2010 | Smith et al. |
| 2010/0168099 | A1 | 7/2010 | Falco et al. |
| 2010/0190771 | A1 | 7/2010 | Claffey et al. |
| 2010/0209506 | A1 | 8/2010 | Eisenreich |
| 2010/0260716 | A1 | 10/2010 | Stohr et al. |
| 2010/0310547 | A1 | 12/2010 | Soliven |
| 2010/0322900 | A1 | 12/2010 | Tarcic et al. |
| 2011/0015132 | A1 | 1/2011 | Zaragoz et al. |
| 2011/0027219 | A1 | 2/2011 | Tarcic et al. |
| 2011/0034508 | A1 | 2/2011 | Hayardeny |
| 2011/0112141 | A1 | 5/2011 | Frenkel |
| 2011/0118308 | A1 | 5/2011 | Frenkel et al. |
| 2011/0217295 | A1 | 9/2011 | Haviv et al. |
| 2011/0218179 | A1 | 9/2011 | Haviv et al. |
| 2011/0218203 | A1 | 9/2011 | Kaye et al. |
| 2011/0251235 | A1 | 10/2011 | Patashnik et al. |
| 2012/0010238 | A1 | 1/2012 | Piryatinsky et al. |
| 2012/0010239 | A1 | 1/2012 | Fristedt |
| 2012/0142730 | A1 | 6/2012 | Tarcic et al. |
| 2012/0142748 | A1 | 6/2012 | Muthuppalaniappan et al. |
| 2012/0225124 | A1 | 9/2012 | Safadi et al. |
| 2012/0252758 | A1 | 10/2012 | Pettersson et al. |
| 2012/0302600 | A1 | 11/2012 | Patashnik et al. |
| 2013/0028866 | A1 | 1/2013 | Gilgun et al. |
| 2013/0029916 | A1 | 1/2013 | Gilgun et al. |
| 2013/0096158 | A1 | 4/2013 | Hallak et al. |
| 2013/0184310 | A1 | 7/2013 | Haviv et al. |
| 2013/0217724 | A1 | 8/2013 | Ioffe et al. |
| 2013/0259856 | A1 | 10/2013 | Kaye |
| 2013/0272996 | A1 | 10/2013 | Tarcic et al. |
| 2013/0303569 | A1 | 11/2013 | Bar-Zohar |
| 2013/0324574 | A1 | 12/2013 | Kaye et al. |
| 2013/0345256 | A1 | 12/2013 | Laxer |
| 2013/0345257 | A1 | 12/2013 | Hahn et al. |
| 2014/0017226 | A1 | 1/2014 | Kaye et al. |
| 2014/0018386 | A1 | 1/2014 | Sarfati et al. |
| 2014/0024678 | A1 | 1/2014 | Safadi et al. |
| 2014/0045886 | A1 | 2/2014 | Martino |
| 2014/0045887 | A1 | 2/2014 | Martino |
| 2014/0051723 | A1 | 2/2014 | Piryatinsky et al. |
| 2014/0057883 | A1 | 2/2014 | Tarcic et al. |
| 2014/0105850 | A1 | 4/2014 | Tarcic et al. |
| 2014/0107154 | A1 | 4/2014 | Filippi et al. |
| 2014/0128430 | A1 | 5/2014 | Frenkel |
| 2014/0171647 | A1 | 6/2014 | Frenkel et al. |
| 2014/0235670 | A1 | 8/2014 | Tarcic et al. |
| 2014/0271878 | A1 | 9/2014 | Frenkel |

FOREIGN PATENT DOCUMENTS

| | | |
|---|---|---|
| EP | 1095021 | 9/2003 |
| EP | 1511732 | 12/2006 |
| EP | 1720531 | 4/2011 |
| WO | WO 99/55678 | 11/1999 |
| WO | WO 00/03991 | 1/2000 |
| WO | WO 00/03992 | 1/2000 |
| WO | WO 03/106424 | 12/2003 |
| WO | WO 2005/074899 | 8/2005 |
| WO | WO 2007/100770 | 9/2007 |
| WO | WO 2007/146331 | 12/2007 |
| WO | WO 2008/085484 | 7/2008 |
| WO | WO 2011/014255 | 2/2011 |
| WO | WO 2014/152009 | 9/2014 |

OTHER PUBLICATIONS

Communication in Response to Sep. 20, 2011 Office Action filed with the U.S. Patent and Trademark Office on Jan. 21, 2013 in connection with U.S. Appl. No. 12/804,795.

Final Office Action issued by the U.S. Patent and Trademark Office on Mar. 26, 2013 in connection with U.S. Appl. No. 12/804,795.

Communication in Response to Mar. 26, 2013 Final Office Action filed with the U.S. Patent and Trademark Office on Jun. 26, 2013 in connection with U.S. Appl. No. 12/804,795.

Amendment in Response to Mar. 26, 2013 Final Office Action filed with the U.S. Patent and Trademark Office on Jul. 18, 2013 in connection with U.S. Appl. No. 12/804,795.

Notice of Allowance issued on Aug. 8, 2013 by the U.S. Patent and Trademark Office in connection with U.S. Appl. No. 12/804,795.

Office Action issued on Mar. 26, 2013 by the Chinese Patent Office in connection with Chinese Patent Application No. 201080039833.9 (incl. English language translation).

Office Action issued on Sep. 22, 2013 by the Chinese Patent Office in connection with Chinese Patent Application No. 201080039833.9 (incl. English language translation).

Response to Sep. 22, 2013 Office Action filed Dec. 9, 2013 in connection with Chinese Patent Application No. 201080039833.9.

Amendment in Response to Mar. 26, 2013 Office Action filed with the Chinese Patent Office on Aug. 9, 2013 in connection with Chinese Patent Application No. 20108003983.9.

European Search Report issued on Jan. 19, 2013 in connection with European Patent Application No. 10804826.5.

Office Action issued on Nov. 8, 2013 in connection with European Patent Application No. 10804826.5.

Official Action issued on Nov. 14, 2013 in connection with Eurasian Patent Application no. 201270221 (including English language translation).

Lowenberg et al. (2013) "Novel Targets for Inflammatory Bowel Disease Therapeutics" Curr. Gastroenterol Rep., vol. 15: 311, pp. 1-6.

PCT International Search Report issued Sep. 7, 2010 in connection with PCT International Application No. PCT/US2010/02129.

PCT International Preliminary Report on Patentability issued Jan. 31, 2012 in connection with PCT International Application No. PCT/US2010/002129.

Written Opinion of the International Searching Authority issued Sep. 7, 2010 in connection with PCT International Application No. PCT/US2010/02129.

Supplementary European Search Report issued Jan. 18, 2013 in connection with European Patent Application No. 10804826.5.

Office Action issued by the U.S. Patent and Trademark Office on Jun. 27, 2012 in connection with U.S. Appl. No. 12/804,795.

Communication in Response To Jun. 27, 2012 Office Action filed with the U.S. Patent and Trademark Office on Jul. 27, 2012 in connection with U.S. Appl. No. 12/804,795.

Mar. 26, 2013 Final Office Action issued in connection with U.S. Appl. No. 12/804,795.

ClinicalTrials.gov [Internet]. Bethesda (MD): National Library of Medicine (US). http://www.clinicaltrials.gov/ct2/show/NCT00737932?term=Crohns&recr=Open&rank=2.

EMEA 2007. Points to consider on clinical investigation of medicinal products for the management of Crohn's disease. CPMP/EWP/2284/99 Rev.1, dated Jul. 24, 2008.

EMEA 2008. Guideline on the Development of New Medicinal Product for the Treatment of Crohn's Disease. CPMP/EWP/2284/99 Rev. 1.

Guindi and Ridell (2004) "Indeterminate Colitis" Journal of Clinical Pathology, 54:1233-1244.

Friedman and Blumberg (2001) Inflammatory Bowel Disease. In: Braunwald E. et al., Harrison's Principles of Internal Medicine. New York: McGraw-Hill Professional, 1679-92.

Hendrickson et al. (2002) Clinical aspects and pathophysiology of inflammatory bowel disease. Clin Microbiol Rev 15:79-94.

Teva Press Release, (Sep. 18, 2008) "Laquinimod Demonstrated Significant and sustained Impact on Multiple Sclerosis Disease Activity".

(56) References Cited

OTHER PUBLICATIONS

Tuvesson et al. (2005) "Cytochrome P450 3A4 is the Major Enzyme Responsible for the Metabolism of Laquinimod . . . " Drug Metabolism and Disposition. 33(6):866-872.

Wen Z. (2004) "Inflammatory bowel disease: autoimmune or immune-mediated pathogenesis?" Clin Develop Immunol 11:195-204.

Wu George et al. "Crohn Disease." Emedicine, updated Mar. 17, 2010, retrieved Jul. 27, 2010, available from http://emedieine.medscape.com/article/172940-overview.

Reagan-Shaw et al. (2007) "Dose translation from animal to human sturdies revisited" FASEB J 22:659-661.

"Guidance for Industry—Estimating the Maximum Safe Starting Dose in Initial Clinical Trials . . . " U.S. Department of Health and Human Services 2005.

Dec. 1, 2014 Written Argument and Amendment filed with the Japanese Patent Office in connection with Japanese Patent Application No. 2012-522812, national stage of PCT International Application No. PCT/US2010/002129.

Nov. 17, 2014 Communication Pursuant to Article 94(3) EPC issued by the European Patent Office in connection with European Patent Application No. 10804826.5, regional stage of PCT International Application No. PCT/US2010/002129.

Jan. 19, 2015 Response to Nov. 17, 2014 Communication Pursuant to Article 94(3) filed with the European Patent Office in connection with European Patent Application No. 10804826.5, regional stage of PCT International Application No. PCT/US2010/002129.

Oct. 31, 2014 Official Action issued by the Eurasian Patent Office in connection with Eurasian Patent Application No. 201270221, regional stage of PCT International Application No. PCT/US2010/002129 (including English translation).

Aug. 1, 2014 Decision of Rejection issued by the Chinese Patent Office in connection with Chinese Patent Application No. 201080039833.9, national stage of PCT International Application No. PCT/US2010/002129 (including English Summary).

PCT International Preliminary Report on Patentability issued Aug. 5, 2014 in connection with PCT International Application No. PCT/US2013/024356.

Written Opinion of the International Searching Authority mailed Apr. 9, 2013 in connection with PCT International Application No. PCT/US2013/024356.

Aug. 12, 2013 Response to the Mar. 26, 2013 First Office Action filed with the Chinese Patent Office in connection with Chinese Patent Application No. 201080039833.9.

Apr. 11, 2014 Official Action issued by the Eurasian Patent Office in connection with Eurasian Patent Application No. 201270221.

Aug. 8, 2014 Response to Apr. 11, 2014 Official Action filed with the Eurasian Patent Office in connection with Eurasian Patent Application No. 201270221.

Mar. 17, 2014 Response to Nov. 8, 2013 Office Action filed with the European Patent Office in connection with European Patent Application No. 10804826.5.

Jul. 29, 2014 Office Action issued by the Japanese Patent Office in connection with Japanese Patent Application No. 2012-522812 (w/ English translation).

Wu et al., (2010) "Crohn Disease", Emedicine, updated Mar. 17, 2010, retrieved on Oct. 24, 2014, available from http://emedicine.medscape.corniarticle/172940-overview.

* cited by examiner

Efficacy – Remissions by Week

Efficacy – Response 100 by Week

USE OF LAQUINIMOD FOR TREATING CROHN'S DISEASE PATIENTS WHO FAILED FIRST-LINE ANTI-TNF THERAPY

This application claims benefit of U.S. Provisional Application No. 61/595,006, filed Feb. 3, 2012, the entire content of which is hereby incorporated by reference herein.

Throughout this application various publications are referenced. The disclosures of these publications in their entireties are hereby incorporated by reference into this application in order to more fully describe the state of the art to which this invention pertains.

BACKGROUND

Crohn's disease (CD) and Ulcerative Colitis (UC) are the two major types of Inflammatory Bowel Disease (IBD)—a generic classification for a group of nonspecific, idiopathic inflammatory disorders of the gastrointestinal (GI) tract which also includes Indeterminate Colitis (IC). Indeterminate Colitis refers to the up to 15% of IBD cases where distinguishing between CD and UC is impossible. (Kasper, 2008) Both CD and UC tend to be chronic in nature and run a course characterized by exacerbations and remissions.

CD may occur in any part of the GI tract, but most commonly affects the distal ileum and colon. It is characterized by transmural inflammation of the gastrointestinal wall, interspersed with "skip" areas of normal tissue, leading to the characteristic endoscopic and radiographic appearance of the disease. In about half the cases, biopsy specimens reveal the pathognomonic histology of noncaseating granulomas (Friedman, 2001).

Although CD usually presents as acute or chronic bowel inflammation, the inflammatory process evolves toward one or two patterns of disease: a fibrostenotic-obstructing pattern or a penetrating-fistulous pattern, each with different treatments and prognoses (Friedman, 2001).

Even though the most common initial presentation of Crohn's disease is purely inflammatory, without fistulizng or perforating complications, more than 70% of CD patients progress to a more complicated disease course within 10 years of diagnosis. More than one-third of these patients develop a distinct fibrostenosing phenotype that manifests by progressive narrowing of the bowel lumen with the potential of intestinal obstruction. It is currently unknown which CD patients will develop a fibrostenotic disease phenotype and in what time frame these changes may occur (Rieder, 2011). Fibrostenotic Crohn's disease does not respond to medical therapy and requires endoscopic or surgical treatment (Foehlich, 2007).

The characteristic inflammatory presentation of Crohn's disease is of abdominal pain, diarrhea, fever and weight loss which may be complicated by intestinal fistulization, obstruction, or both. Fistula formation may occur to the adjacent bowel, the skin, the urinary bladder, or other locations. Obstruction, if present, is initially intermittent due to bowel wall edema and spasm; further progression may lead to chronic scarring and stricture formation. Perianal disease is common and may manifest as anal fissure, perianal fistula, or abscess (Friedman, 2001; Wu, 2007).

Extra-intestinal manifestations may also occur and include joint inflammation (e.g., peripheral arthritis, ankylosing spondylitis), skin lesions (e.g., erythema nodosum, pyoderma gangrenosum), ocular involvement (e.g., iritis, uveitis) and liver disorders (e.g., hepatic steatosis, primary sclerosing cholanitis) (Friedman, 2001; Wu, 2007).

The incidence of CD varies within different geographic areas. Northern countries such as the US, UK, Norway and Sweden have the highest rates. The incidence of CD in the US is approximately 7 per 100,000. Countries in southern Europe, South Africa and Australia have lower incidence rates of 0.9 to 3.1 per 100,000. The disease is rare in Asia and South America (Friedman, 2001).

The peak age of onset of Crohn's disease occurs between the ages of 15 and 30 years, with a second peak of occurrence between the ages of 60-80 years (Friedman, 2001).

The fundamental cause of CD is unknown. There are four basic factors affecting the pathophysiology of CD: genetics, immune dysregulation, epithelial barrier dysfunction and the constitution of microbial flora. Evidence suggests that genetic predisposition leads to an unregulated intestinal immune response to an environmental, dietary or infectious agent (Friedman, 2001; Wen, 2004). A number of studies suggest that CD is a T-helper 1 (Th-1) mediated disease and that the excessive Th1-cell activity leading to the production of a wide range of proinflammatory cytokines [including interleukin (IL)-1, IL-2 and tumor necrosis factor (TNF)-$\alpha$] and an imbalance between proinflammatory and anti-inflammatory reactivity, is a critical component of CD (Hendrickson, 2002). However, no inciting antigen has been identified.

In the absence of a key diagnostic test, the diagnosis of Crohn's disease is based on endoscopic, radiographic and pathological findings documenting focal, asymmetric transmural or granulomatous features. Laboratory abnormalities include non-specific markers of inflammation such as elevated sedimentation rate and C-reactive protein (CRP). In more severe cases, finding may include hypoalbuminemia, anemia, and leukkocytosis (Friedman, 2001; Wu, 2007).

There is no definitive treatment or cure for CD. The major therapeutic goals are the reduction of signs and symptoms, induction and maintenance of remission and most importantly, the prevention of disease progression and complications.

Sulfasalazine and other 5-aminosalicylic acid agents, antibiotics such as metronidazole and ciprofloxacin, corticosteroids, immunosupressors such as azathioprine and 6-mercaptopurine and biologic agents such as anti-TNF$\alpha$ agents and anti-integrins that prevent leukocyte infiltration have shown to be useful in the induction of remission and/or in its maintenance (Targan, 1977; Hanauer, 2002; Colombel, 2007; Ghosh, 2003; Sandborn, 2005; Schreiber, 2005; Schreiber, 2007; Kozuch, 2008). Many of these medicinal products, however, are only moderately efficacious and are associated with challenging side effects (Hommes, 2003; Thomas, 2004; Colombel, 2004; Van Assche, 2005; Vermeire, 2003; Sweetman, 2006). In addition, the newer biologic agents have a relatively inconvenient parenteral route of administration.

Loss of response to anti-TNF$\alpha$s at 12 months of therapy occurs in 23-46% of patients when judged by dose intensification, or 5-13% when gauged by drug discontinuation rates. The management of loss of response should allow for a period of watchful waiting as quite often the patients' symptoms may resolve without alteration of therapy. If they do not, then identifying the correct mechanism responsible for clinical deterioration is prudent. Once symptoms are ascertained to arise from inflammatory IBD activity, drug level and antidrug antibody measurement can then help distinguish between non-adherence to therapy, immunogenicity and non-immune clearance of anti-TNF$\alpha$, or an un-chequered inflammation despite adequate anti-TNF$\alpha$ levels. The latter finding may be best addressed by a switch to another class of immunomodulators, whereas a low drug level should probably be managed by dose intensification or a switch to another anti-TNFα (S. Ben-Horin; Alimentary Pharmacology & Therapeutics. 2011; 33(9):987-995.).

There is, therefore, a definite need for alternative therapies with better risk-benefit profiles and a more convenient route of administration than the currently available options.

Disclosed is a method of treating Crohn's disease using laquinimod. Laquinimod is a novel synthetic compound with high oral bioavailability, which has been suggested as an oral formulation for Relapsing Remitting Multiple Sclerosis (MS).

Laquinimod and its sodium salt form are described, for example, in U.S. Pat. No. 6,077,851.

SUMMARY OF THE INVENTION

Figure 1:
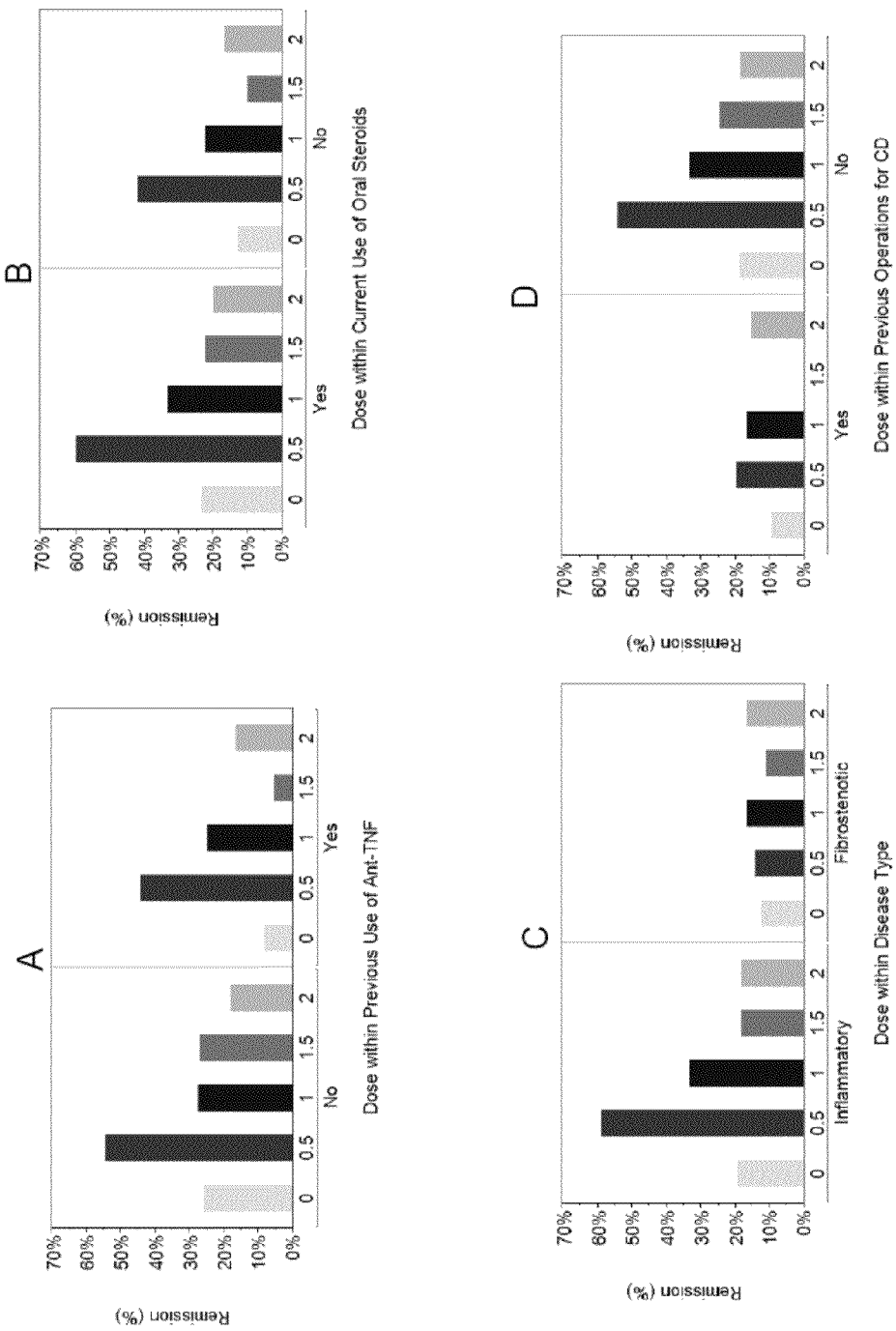
FIG. 1 is a graphical representation of the experimental results from Example 2. In anti-TNF refractory patients, 0.5 mg/day laquinimod was robustly effective. 1 mg/day laquinimod was also effective relative to placebo.

This application provides for a method of treating a human patient afflicted with anti-TNFα refractory Crohn's disease, the method comprising periodically administering to the patient an amount of laquinimod or pharmaceutically acceptable salt thereof effective to treat the patient.

This application also provides for a method of treating a human patient afflicted with non-fibrostenotic Crohn's disease, the method comprising periodically administering to the patient an amount of laquinimod or pharmaceutically acceptable salt thereof effective to treat the patient.

This application also provides for a method of treating a human patient afflicted with Crohn's disease, the method comprising periodically administering to the patient an amount of laquinimod or pharmaceutically acceptable salt thereof effective to treat the patient, wherein the patient's Crohn's disease had not been surgically treated.

This application also provides for the use of laquinimod for treating a patient afflicted with anti-TNFα refractory Crohn's disease.

This application also provides for a pharmaceutical composition comprising laquinimod for use in treating a subject afflicted with anti-TNFα refractory Crohn's disease.

This application also provides for the use of laquinimod for treating a patient afflicted with non-fibrostenotic Crohn's disease.

This application also provides for a pharmaceutical composition comprising laquinimod for use in treating a subject afflicted with non-fibrostenotic Crohn's disease.

This application also provides for the use of laquinimod for treating a patient afflicted with Crohn's disease, wherein the Crohn's disease had not been surgically treated.

This application also provides for a pharmaceutical composition comprising laquinimod for use in treating a patient afflicted Crohn's disease, wherein the Crohn's disease had not been surgically treated.

This application also provides for a method of inducing or maintaining clinical remission in a human patient afflicted with Crohn's disease comprising periodically administering to the patient an amount of laquinimod effective to induce or maintain clinical remission in the patient, which amount of laquinimod is less than 0.5 mg/day.

This application also provides for the use of a daily dose of less than 0.5 mg/day laquinimod for inducing or maintaining clinical remission in a human patient afflicted with Crohn's disease.

This application also provides for a pharmaceutical composition comprising a unit dose of less than 0.5 mg laquinimod for inducing or maintaining clinical remission in a human patient afflicted with Crohn's disease.

DETAILED DESCRIPTION OF THE INVENTION

This application provides for a method of treating a human patient afflicted with anti-INFα refractory Crohn's disease, the method comprising periodically administering to the patient an amount of laquinimod or pharmaceutically acceptable salt thereof effective to treat the patient.

In an embodiment, the Crohn's disease is non-fibrostenotic Crohn's disease. In another embodiment, the Crohn's disease is inflammatory Crohn's disease.

In one embodiment, the Crohn's disease is steroid refractory Crohn's disease. In another embodiment, the patient's Crohn's disease had not been surgically treated.

In another embodiment, the Crohn's disease is refractory to anti-INFα treatment using infliximab, adalimimab, certolizumab or natalizumab. In yet another embodiment, the patient is naïve to anti-INFα treatment.

This application also provides for a method of treating a human patient afflicted with non-fibrostenotic Crohn's disease, the method comprising periodically administering to the patient an amount of laquinimod or pharmaceutically acceptable salt thereof effective to treat the patient.

In one embedment, the non-fibrostenotic Crohn's disease is inflammatory Crohn's disease. In another embodiment, the Crohn's disease is steroid refractory Crohn's disease. In yet another embodiment, the patient's Crohn's disease had not been surgically treated.

This application also provides for a method of treating a human patient afflicted with Crohn's disease, the method comprising periodically administering to the patient an amount of laquinimod or pharmaceutically acceptable salt thereof effective to treat the patient, wherein the patient's Crohn's disease had not been surgically treated. In one embodiment, the Crohn's disease is steroid refractory Crohn's disease.

In one embodiment, the amount of laquinimod is effective to reduce a symptom of Crohn's disease in the subject, induce clinical response, induce or maintain clinical remission, inhibit disease progression, or inhibit a disease complication in the subject. In another embodiment, the pharmaceutically acceptable salt of laquinimod is laquinimod sodium.

In one embodiment, the periodic administration is oral. In another embodiment, the amount is administered by a unit dose of 0.5 mg of laquinimod. In another embodiment, the amount is administered by a unit dose of 0.25 mg of laquinimod. In another embodiment, the periodic administration is daily administration.

In an embodiment, the amount of laquinimod is effective to induce clinical remission in the patient. In another embodiment, the amount of laquinimod is effective to maintain clinical remission in the patient. In yet another embodiment, the amount of laquinimod is effective to induce and maintain clinical remission in the patient.

In one embodiment, the amount of laquinimod is 0.1-1.0 mg/day. In another embodiment, the amount of laquinimod is 0.1-0.75 mg/day. In another embodiment, the amount of laquinimod is 0.2-1.0 mg/day. In another embodiment, the amount of laquinimod is 0.25-1.0 mg/day. In another embodiment, the amount of laquinimod is 0.2-0.5 mg/day. In another embodiment, the amount of laquinimod is 0.25-0.5 mg/day. In another embodiment, the amount of laquinimod is 0.3-0.7 mg/day. In another embodiment, the amount of laquinimod is 0.25 mg/day. In another embodiment, the amount of laquinimod is 0.5 mg/day. In another embodiment, the amount of laquinimod is 1.0 mg/day.

In an embodiment, the laquinimod is administered as adjunct therapy with an other Crohn's disease treatment. In another embodiment, the other Crohn's disease treatment is oral steroids, 6-Mercaptopurine, azathioprine, and methotrexate.

This application also provides for the use of laquinimod for treating a patient afflicted with anti-TNFα refractory Crohn's disease. This application further provides for a pharmaceutical composition comprising laquinimod for use in treating a subject afflicted with anti-TNFα refractory Crohn's disease.

This application also provides for the use of laquinimod for treating a patient afflicted with non-fibrostenotic Crohn's disease. This application further provides for a pharmaceutical composition comprising laquinimod for use in treating a subject afflicted with non-fibrostenotic Crohn's disease.

This application also provides for the use of laquinimod for treating a patient afflicted with Crohn's disease, wherein the Crohn's disease had not been surgically treated. This application further provides for a pharmaceutical composition comprising laquinimod for use in treating a patient afflicted Crohn's disease, wherein the Crohn's disease had not been surgically treated.

This application also provides for a method of inducing or maintaining clinical remission in a human patient afflicted with Crohn's disease comprising periodically administering to the patient an amount of laquinimod effective to induce or maintain clinical remission in the patient, which amount of laquinimod is less than 0.5 mg/day.

In an embodiment, the amount of laquinimod is effective to induce clinical remission in the patient. In another embodiment, the amount of laquinimod is effective to maintain clinical remission in the patient. In yet another embodiment, the amount of laquinimod is effective to induce and maintain clinical remission in the patient.

In one embodiment, the amount of laquinimod 0.1-0.45 mg/day. In another embodiment, the amount of laquinimod is 0.1 mg/day. In another embodiment, the amount of laquinimod is 0.2 mg/day. In another embodiment, the amount of laquinimod is 0.25 mg/day. In another embodiment, the amount of laquinimod is 0.3 mg/day. In another embodiment, the amount of laquinimod is 0.4 mg/day. In another embodiment, the amount of laquinimod is 0.45 mg/day.

This application also provides for the use of a daily dose of less than 0.5 mg/day laquinimod for inducing or maintaining clinical remission in a human patient afflicted with Crohn's disease. This application further provides for a pharmaceutical composition comprising a unit dose of less than 0.5 mg laquinimod for inducing or maintaining clinical remission in a human patient afflicted with Crohn's disease.

For the foregoing embodiments, each embodiment disclosed herein is contemplated as being applicable to each of the other disclosed embodiments. In addition, the elements recited in the pharmaceutical composition embodiments can be used in the method and use embodiments described herein, and vice versa.

A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, each of which is hereby incorporated by reference into this application.

A dosage unit may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO/2007/146248, each of which is hereby incorporated by reference into this application.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Terms

As used herein, and unless stated otherwise, each of the following terms shall have the definition set forth below.

As used herein, "laquinimod" means laquinimod acid or a pharmaceutically acceptable salt thereof.

As used herein, a subject or a patient at "baseline" is a subject or patient prior to initiating periodic administration of laquinimod.

As used herein, "about" in the context of a numerical value or range means±10% of the numerical value or range recited or claimed.

An "amount" or "dose" of laquinimod as measured in milligrams refers to the milligrams of laquinimod acid present in a preparation, regardless of the form of the preparation.

As used herein, a "loading dose" refers to an initial higher dose of a drug that may be given at the beginning of a course of treatment before dropping down to a lower "intended dose" or "maintenance dose".

As used herein "afflicted", as in a patient afflicted with a disease or a condition, means a patient who has been affirmatively diagnosed to have the disease or condition. For example, a patient afflicted with anti-TNFα refractory Crohn's disease means a patient who has been affirmatively diagnosed to have anti-TNFα refractory Crohn's disease. The diagnosis of the disease or condition can be effected using any of the appropriate methods known in the art. For example anti-TNFα refractory Crohn's disease can be diagnosed by administering to a Crohn's disease patient anti-TNFα treatment and assessing whether and how the patient responds. Thus, in an embodiment of the present invention the method includes the step of determining whether a patient is an anti-TNFα refractory Crohn's disease patient, whether the patient is non-fibrostenotic Crohn's disease patient, whether the patient is a steroid refractory Crohn's disease patient, or whether the patient is a Crohn's disease patient whose Crohn's disease had not been surgically treated.

A "symptom" associated with a disease or disorder includes any clinical or laboratory manifestation associated with the disease or disorder and is not limited to what the subject can feel or observe.

As used herein, "Crohn's Disease Activity Index" or "CDAI" is a research tool developed by WR Best and colleagues from the Midwest Regional Health Center in Illinois, in 1976 (Best, 1976) to quantify the symptoms of patients with Crohn's disease. The index is the most widely used instrument for evaluation of Crohn's disease activity (Best, 1976; Best, 1979; Sandborn, 2002) and consists of eight factors/variables.

The eight variables are summed after adjustment with a weighting factor. The components of the CDAI and weighting factors are shown in the following table 1:

TABLE 1

| Clinical or laboratory variable | Weighting factor |
|---|---|
| Number of liquid or soft stools (sum of each day for 7 days) | x 2 |
| Abdominal pain (graded from 0-3 on severity) (sum of each day for 7 days) | x 5 |
| General well being, subjectively assessed from 0 (well) to 4 (terrible) (sum of each day for 7 days) | x 7 |
| Presence of Crohn's disease complications | x 20 |
| Use of dyphenoxylate or loperamide for diarrhea during the past week (0 = no, 1 = yes) | x 30 |
| Presence of an abdominal mass (0 as none, 2 as questionable, 5 as definite) | x 10 |
| Absolute deviation of Hematocrit from 47% in men and 42% in women | x 6 |
| Percentage deviation from standard weight | x 1 |

The first 4 of these variables and the presence of fever above 37.8° C., are self-reported in subject diaries, the remaining 4 are assessed at the study visit. Height and standard weight assessment are based on standard height-weight tables.

Total CDAI scores range from 0 to approximately 600 where the higher the score, the more active the disease. A CDAI score of less than 150 points denotes "clinical remission" of the Crohn's disease, of between 150 to 219 points denotes "active mild Crohn's disease", of between 220 to 450 points denotes "active moderate Crohn's disease" and of more than 450 points denotes "active severe Crohn's disease".

As used herein "anti-INFα refractory Crohn's disease" means Crohn's disease which is unresponsive or resistant to anti-INFα therapy. In particular, patients are afflicted with anti-INFα refractory Crohn's disease if they have no initial response to two clinically approved doses of anti-INFα therapy or respond initially but lose responsiveness or develop intolerance within one year. Crohn's disease patients may also be refractory to specific anti-INFα therapy (Mannon, 2007).

"Clinical response" means that the subject's Crohn's disease symptoms have decreased in severity and/or in number. "Clinical remission" means that the subject's Crohn's disease symptoms have decreased in severity and/or in number to below a defined level, e.g., below 150 points on the CDAI scale. "Clinical remission" and "clinical response" may be measured in accordance with the EMEA draft guidelines on the development of new medicinal products for the treatment of Crohn's disease. The EMEA guidelines define "clinical remission" as reduction in CDAI score to a total score below 150 points and "clinical response" as if remission has been achieved or a reduction of at least 100 points in the total CDAI score has been observed, compared to baseline at the end of the treatment period (EMEA, 2007).

"Indeterminate Colitis" or "IC" is used clinically in patients with some form of Inflammatory Bowel Disease in whom a definite diagnosis of either Ulcerative Colitis (UC) or Crohn's Disease (CD) has not been made, either on colonoscopy or colonic biopsy before colectomy. Although some patients diagnosed with Indeterminate Colitis go on to develop UC or CD, studies have shown that over a median follow up period of 10 years, many patients retain diagnosis of Indeterminate Colitis. (Guindi, 2004)

"Inhibition" of disease progression or disease complication in a subject means preventing or reducing the disease progression and/or disease complication in the subject.

As used herein, "C-reactive protein" or "CRP" is an inflammatory mediator whose levels are raised under conditions of acute inflammatory recurrence and rapidly normalize once the inflammation subsides. Crohn's disease may be characterized according to disease behavior: predominantly nonstricturing nonpenetrating (inflammatory), stricturing or penetrating (Silverberg, 2005). The origin of symptoms such as diarrhea, fatigue, or abdominal pain (affects the CDAI score) may be multifactorial and does not necessarily correlate with the existence of prominent inflammatory lesions of the gastrointestinal (GI) tract. Predominantly nonstricturing nonpenetrating (inflammatory) Crohn's disease may be characterized by high CRP levels. Therefore the CRP may serve as a surrogate marker to monitor inflammatory disease activity and response to treatment (Solem, 2005; Denis, 2007; Chamouard, 2006).

As used herein, "calprotectin" is a calcium and zinc binding anti-microbial protein released by granulocytes. This protein can be detected in stool and its concentration reflects the number of polymorphonuclear leukocytes (PMN), migrating into the gut lumen. It is therefore considered a bio-marker for intestinal inflammation.

As used herein, "effective" when referring to an amount of laquinimod refers to the quantity of a laquinimod that is sufficient to yield a desired therapeutic response without undue adverse side effects (such as toxicity, irritation, or allergic response) commensurate with a reasonable benefit/risk ratio when used in the manner of this invention.

As used herein, "treating" encompasses, e.g., inducing inhibition, regression, or stasis of the disorder.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "5-10%" includes 5.0%, 5.1%, 5.2%, 5.3%, 5.4% etc. up to 10.0%.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Clinical Trial (Phase IIa)—Assessment of Oral Laquinimod in Active Moderate to Severe Crohn's Disease (CD-LAQ-201)

A phase IIa, multicenter, randomized, double-blind, placebo-controlled, sequential cohorts, dose range finding study was conducted to evaluate escalating doses of Laquinimod in active moderate to severe Crohn's disease.

Study Title

A Phase IIa, Multicenter, Randomized, Double-Blind, Placebo-Controlled, Sequential Cohorts, Dose Range Finding Study to Evaluate the Safety, Tolerability and Clinical Effect of Escalating Doses of Laquinimod in Active Moderate to Severe Crohn's disease.

Participating Countries and Number of Sites

Europe (Belgium, France, Italy, Netherlands, Spain, Poland and UK), Israel and South Africa in approximately 50 sites.

Number of Subjects

There were 4 distinct sequential cohorts with approximately 45 subjects for each of the cohorts, randomized in a 2:1 ratio (~30 subjects on laquinimod and ~15 on placebo). Overall up to ~180 Crohn's disease patients are enrolled. Of these 117 patients received laquinimod and 63 pateitns received placebo.

Investigational Medicinal Product (IMP) & Dosage

One or more capsules containing laquinimod 0.5 mg or matching placebo were administered orally once daily:

$1^{st}$ cohort—laquinimod 0.5 mg (1×0.5) or matching placebo;

$2^{nd}$ cohort—laquinimod 1.0 mg (2×0.5) or matching placebo;

$3^{rd}$ cohort—laquinimod 1.5 mg (3×0.5) or matching placebo; and $4^{th}$ cohort—laquinimod 2.0 mg (4×0.5) or matching placebo.

The 0.5 mg laquinimod capsules were prepared using 0.534 mg of laquinimod sodium per capsule (which is equivalent to 0.5 mg of laquinimod acid). The capsules were prepared using a blend proportional to the 0.6 mg capsules described in PCT International Application No. PCT/US2007/013721 (WO 2007/146248). The capsules were prepared according to the method described in PCT International Application No. PCT/US2007/013721 (WO 2007/146248), which is hereby incorporated by reference into this application.

A loading dose regimen of double the maintenance/intended dose was given during the first two days of study drug treatment. Thereafter, starting on day 3, the daily maintenance/intended dose was administered.

Table 2 summarizes the number of capsules and total dose which were administered daily for each of the 4 study cohorts, at different time points throughout the treatment period. "BID" indicates that the dose was administered twice daily. "QD" indicates that the dose was administered once daily.

TABLE 2

| Cohort | Day 1 | | Day 2 | | Day 3 onwards | |
|---|---|---|---|---|---|---|
| | 0.5 mg/plc capsules/day | Dose/day | 0.5 mg/plc capsules/day | Dose/day | 0.5 mg/plc capsules/day | Dose/day |
| 1 | 1 + 1 (BID) | 1 mg/placebo | 1 + 1 (BID) | 1 mg/placebo | 1 (QD) | 0.5 mg/placeo |
| 2 | 2 + 2 (BID) | 2 mg/placebo | 2 + 2 (BID) | 2 mg/placebo | 2 (QD) | 1 mg/placeo |
| 3 | 3 + 3 (BID) | 3 mg/placebo | 3 + 3 (BID) | 3 mg/placebo | 3 (QD) | 1.5 mg/placeo |
| 4 | 4 + 4 (BID) | 4 mg/placebo | 4 + 4 (BID) | 4 mg/placebo | 4 (QD) | 2 mg/placeo |

Subjects are required to maintain CDAI diary cards for each day of the screening period and, if randomized, on each day of the treatment and follow-up period. The scores obtained from the seven consecutive diaries completed prior to the baseline visit and to each of weeks 1, 2, 4, 6, 8 and 12 contribute to a total CDAI score at each of the time points.

Allowed previous standard of care treatment was kept stable throughout the study (including the follow-up period, as defined herein).

Study Duration

Each Cohort (Dose Group) is Evaluated for Up to 14 Weeks

Screening: between 1-2 weeks

Treatment period: 8 weeks

Follow-up period: 4 weeks

Study Population

Moderate to severe Crohn's disease (CD) subjects as determined by a Crohn's Disease Activity Index (CDAI) score of 220-450 (inclusive).

Study Design

This Phase IIa, randomized, double-blind, placebo-controlled, sequential cohorts, dose range finding study to assess the safety tolerability and clinical effect of escalating dose of laquinimod in active moderate to severe Crohn's disease was the first study to assess the safety, tolerability and efficacy of laquinimod in active CD subjects.

This study investigates laquinimod doses at 0.5, 1.0, 1.5 and 2.0 mg daily. Each dose was studied sequentially in a distinct cohort.

Subjects were assessed for study eligibility 1 to 2 weeks prior to baseline.

Approximately 45 eligible subjects are assigned to each cohort. Subjects were randomized in a 2:1 ratio for either of the following treatment arms:
1. Oral laquinimod (~30 subjects).
2. Matching oral placebo (~15 subjects).

Each successive cohort is screened/randomized only when the two conditions below have been met:
1. Randomization of at least 45 subjects for the preceding cohort and closure of screening and randomization of the preceding cohort.
2. Decision of a safety committee to proceed to the next dose level.

This decision was based on data review of at least 15 subjects who have completed at least 4 weeks of treatment in the preceding cohort, as well as all other data obtained in the study for any of the preceding cohorts.

All study investigators were informed when screening and/or randomization are closed for the preceding cohort and opened for the next cohort/dose level. All subjects in screening phase were allowed to be randomized (if eligible) to the preceding cohort or the next cohort, whichever was opened at randomization/baseline visit.

The safety committee may determine at any of these safety evaluations, that a Dose Limiting Toxicity (DLT) has been reached. Criteria for DLT were not predefined and are based solely on the safety committee's best medical judgment.

In case a dose limiting toxicity has been reached the following decision options exist for the safety committee:
1. Complete the current cohort without proceeding to the next dose level/cohort; and
2. Terminate the study immediately.

Scheduled in-clinic visits were conducted at screening, baseline and at weeks 1, 2, 4, 6 and 8. Treatment with laquinimod/placebo were discontinued on visit week 8 and a follow-up/study completion visit was conducted at week 12. Subjects who early-discontinues study drug prior to visit week 8 go to follow-up termination visit within 4 weeks (28 days) of study drug discontinuation.

Unscheduled visits for safety or for any other reason may be conducted at any time during the study.

During the study period the CDAI score was assessed in addition to routine safety laboratory tests and PK analysis.

Based on previous pharmacokinetic studies, laquinimod reaches steady state following approximately 10-12 days of daily maintenance dosing. In order to decrease thee time to steady state and potentially decrease time to response, a loading dose regimen described below was used to allow steady state levels to be reached in approximately 6-7 days.

A loading dose regimen of the study drug was given during the first two days of treatment (day 1/baseline and thereafter). The first loading dose of the study is administered at the site. The loading dose is double the intended dose for the first two days and is administered twice daily (BID) with 12 hour interval between dosing. Thereafter, starting on day 3, the dosing regimen consists of the intended dose once daily (QD) (see Table 1):
1. Day 1 (Baseline): loading dose of the drug (intended dose at 0 hour, at the site and intended dose at 12 hours). Total dose was twice the intended dose.
2. Day 2: loading dose of the study drug (intended dose at 0 hour and intended dose at 12 hours). Total dose was twice the intended dose.
3. Day 3: Intended/maintenance dose of the study drug.

Allowed previous standard of care treatment was kept stable throughout the study (including the follow-up period as defined herein).

PK Analysis

Pharmacokinetic Sub-Study (PK)—Ancillary Study Performed in Subset of Sites

Blood samples for PK analysis—24 h profile—were collected from subjects in the first cohort (0.5 mg/placebo) on week 4.

A single, pre-dose sample was collected from the first cohort (0.5 mg/placebo) on week 1 as part of steady state course assessment.

Population PK Study (PPK)

Blood samples for PPK evaluation were collected at weeks 2 and 8 from all subjects in all cohorts. A pre-dose sample and a single sample at post-dose time range within 0.5 to 6 hours were collected.

Pharmacogenetic Sub-Study

Blood samples for the pharmacogenetic sub-study were collected from all subjects who sign the separate informed consent form and upon Ethics Committee (EC) approval.

Allowed Concomitant Medications During Study

In general the dose of allowed concomitant medication was kept stable throughout the study (including the follow-up period). Any new medication/treatment for CD or dose increase not allowed by the protocol, throughout the study treatment period, results in major protocol violation and was regarded as a treatment failure. Decrease in dose or dose regiment, not allowed by the protocol, also results in major protocol violation.

CD surgery, biologic treatment or new immunosuppressive drugs, throughout the study treatment period, are regarded as treatment failure and results in early treatment discontinuation.

5-ASA Compounds

The use of 5-ASA compounds were kept stable throughout the study.

Antibiotics

The use of antibiotics for the treatment of Crohn's disease was kept stable throughout the trial. Managing acute infections (not related to Crohn's disease) was allowed.

Corticosteroids

The dose of oral corticosteroids remains stable throughout the study:
1. Oral systemic corticosteroids—no more than prenisolone 2.5 mg/day (or equivalent) increase or decrease compared to baseline.
2. Budesonide—no change was permitted compared to baseline.
3. IV or IM corticosteroid dose or corticosteroid enemas were not allowed.

Immunosuppresives

Immunosuppressive treatment allowed by the protocol (AZT/6 MP/MTX) was kept stable throughout the study. Addition of new immunosuppressive drug is not allowed Other
1. Antidiarrehal drugs, analgesics, NSAIDs and topical preparations were allowed (including topical dermatological, ophthalmological or inhale steroids).
2. The use of probiotics was kept stable throughout the study.

Inclusion/Exclusion Criteria

Inclusion Criteria

Subjects must meet all the inclusion criteria to be eligible:
1. Males and females 18-75 years old (inclusive).
2. Subjects diagnosed with Crohn's disease for at least 3 months prior to screening, which has been appropriately documented and supported by endoscopy or radiology (performed within 36 months prior to screening and after surgical resection), or surgery.
3. Moderate to severe Crohn's disease patients as determined by a CDAI score of 220-450 (inclusive).
4. Subjects with C-Reactive Protein (CRP) levels above 5 mg/L at screening or any time between screening to baseline, including at baseline, OR documented endoscopic evidence of mucosal ulcerations within 4 weeks prior to baseline.
   a. Evidence of mucosal ulcerations was defined as the presence of at least 2 ulcers 10 mm.
   b. Documentation includes the endoscopy report with supporting photo or video.
5. Subjects willing and able to provide written, informed consent.

Elevated fecal calprotectin was not required.

Exclusion Criteria

Any of the following excludes the subject from entering the study:
1. Subjects with a diagnosis of Indeterminate Colitis.
2. Subjects with positive results on stool culture for enteric pathogens (*Salmonella, Shigella, Yersinia, Campylobacter* or *Clostridia Difficile* toxin assay), at screening.
3. Subjects who have had bowel surgery within the 3 months prior to screening or with planned elective surgery or hospitalization during the course of the study (that may interfere with study compliance or outcome).
4. Subjects with clinically significant Short Bowel Syndrome.
5. Subjects with clinically significant GI obstructive symptoms.
6. Subjects with intra-abdominal abscess.
7. Subjects with fistula with clinical or radiological evidence of abscess.
8. Subjects with ileostomy, colostomy or who receive parenteral nutrition.
9. Subjects with a clinically significant or unstable medical or surgical condition that, in the Investigator's opinion, would preclude safe and complete study participation, as determined by medical history, physical examinations, ECG, laboratory testing or imaging. Such conditions may include:
   a. A cardiovascular or pulmonary disorder that cannot be well-controlled by standard treatment permitted by the study protocol.
   b. Renal, metabolid or hematological diseases.
   c. Any form of acute or chronic liver disease.
   d. Known human immunodeficiency virus (HIV) positive status.
   e. Systemic infection at screening.
   f. A family history of Long-QT syndrome.
   g. A history of drug and/or alcohol abuse.
   h. A current major psychiatric disorder.
10. Subjects with a ≥2× upper limit of normal (ULN) serum elevation of either of the following at screening: ALT, AST, GGT, ALKP or direct bilirubin.
11. A QTc interval which is >500 msec (according to machine output), obtained from:
    a. Two ECG recordings at screening visit OR
    b. The mean value calculated from 2 baseline ECG recordings.
12. Subjects with history of any malignancy in the last year, prior to screening, excluding basal cell carcinoma.
13. Subjects treated with oral corticosteroids (e.g. prednisolone/budesonide), who have initiated this treatment within less than 4 weeks prior to screening.
14. Subjects treated with more than 20 mg/day of prednisolone (or equivalent) or budesonide >6 mg/day for CD at screening, or whose corticosteroid dosage regimen is not stable for at least 2 weeks prior to baseline. [stable dose defined as 2.5 mg prednisolone (or equivalent) increase or decrease, no change in budesonide and no IV or IM steroid administration, within the last 2 weeks prior to baseline].
15. Subjects treated with 5-ASA who are not on stable dose for at least 2 weeks prior to screening.
16. Subjects treated with antibiotics for CD who are not on a stable dose for at least 2 weeks prior to screening.
17. Subjects treated with 6-MP, AZA or MTX, who have initiated this treatment within 12 weeks prior to screening or who are not on a stable dose for at least 6 weeks prior to screening.
18. Subjects treated with Anti-TNFαs within 4 weeks prior to screening [The percentage of subjects previously treated with anti-TNFα drugs are limited to approximately 60% of subjects randomized for each cohort. All site principle investigators are notified by the Sponsor when the quota of previous treatment with anti-TNFα drugs has been reached for each cohort].
19. Subjects treated with cyclosporine, tacrolimus, mycophenolate mofetil or thalidomide within 2 months prior to screening.
20. Subjects treated with natalizumab within 6 months prior to screening.
21. Subjects who have used any other investigational drugs within 3 months prior to screening.
22. Use of inhibitors of CYP3A4 within 2 weeks prior to base line visit (1 month for fluoxetine).
23. Use of amiodarone within 2 years prior to screening visit.
24. Women who are pregnant or nursing at the time of screening, or who intend to be during the study period.
25. Women of child-bearing potential who do not practice an acceptable method of birth control. Acceptable methods of birth control in this study are: surgical sterilization, intrauterine devices, oral contraceptive, contraceptive patch, long-acting injectable contraceptive, partner's vasectomy, a double-protection method (condom or diaphragm with spermicide).
26. A known drug hypersensitivity that would preclude administration of the study drug, such as hypersensitivity to: mannitol, meglumine or sodium stearyl fumarate.
27. Subjects unable to comply with the planned schedule of study visits and study procedures.

Withdrawal Criteria/Treatment Failure
1. At the direction of the investigator, a subject who fails to respond to the treatment protocol is withdrawn from the study.
2. Rescue therapy for Crohn's disease (any new medication/treatment or dose increase, not allowed by the protocol), throughout the study treatment period, results in major protocol violation and is regarded as a treatment failure.

3. CD Surgery, biologic treatment of new immunosuppressive drugs, throughout the study treatment period, is regarded as treatment failure and results in early treatment discontinuation.

Monitoring Plan and Safety Stopping Rules

In any of the events listed below, the subject's participation in the study is discontinued immediately. The subject is followed until resolution or stabilization of symptoms or lab abnormalities:
1. Any increase in ALT or AST to ≥3 times ULN, combined with either ≥1.5 times ULN elevation of INR or ≥2 times ULN elevation of total bilirubin.
2. Any increase in ALT or AST to 3 times ULN, with the appearance of worsening of fatigue, nausea, vomiting, right upper quadrant pain or tenderness, fever, rash, or eosinophilia.
3. Any increase in Alt or AST to levels ≥5 but <8 times ULN, which is persistent for ≥2 weeks of repeated measurements.
4. Any increase in ALT or AST to levels 8 times ULN.

Outcome Measures

Clinical Effect

The study exploratory efficacy outcome measures were chosen according to the draft EMEA guidelines for the treatment of active Crohn's disease/induction of remission (EMEA, 2007)
1. Proportion of subjects in clinical remission (total CDAI score <150) at weeks 4, 6, 8 and 12 (and were not treatment failures).
2. Proportion of subjects who respond to treatment (decrease from baseline of at least 100 points in CDAI score ore remission) at week 4, 6, 8 and 12.
3. Time to remission.
4. Time to response.
5. C-Reactive Protein (CRP) change from baseline at weeks 2, 4, 6, 8 and 12.
6. Fecal calprotectin change from baseline to weeks 2, 4, 6, 8 and 12.
7. Proportion of subjects with a decrease from baseline of at least 50% in the number of open draining fistulas.

Safety/Tolerability
1. Adverse events (AEs).
2. Clinical laboratory values.
3. Vital signs.
4. ECG.
5. Proportion of subjects who prematurely discontinue treatment.
6. Proportion of subjects who prematurely discontinue treatment due to AEs.
7. Time to premature treatment discontinuation.
8. Time to premature treatment discontinuation due to AEs.

Determination of the Highest Tolerable Dose

At any of the safety evaluations, the safety committee may determine that a Dose Limiting Toxicity (DLT) has been reached. Criteria for DLT were not predefined and were based solely on the safety committee's best medical judgment.

The highest tolerable dose was defined as the dose level below the dose at which no further escalation was permitted, according to the decision of the safety committee.

Pharmacokinetics/Population PK

Steady state parameters ($AUC_{tau}$, $C_{max}$, and $C_{min}$) were calculated for the 0.5 mg dose only (in a subset of sites)

The population approach is used to fit the plasma concentration-time data from all dose groups, if possible. The effect of different covariates on the pharmacokinetics of laquinimod was evaluated in the model (all sites, all cohorts).

Results

Clinical Remission and Response 100

Figure 2:
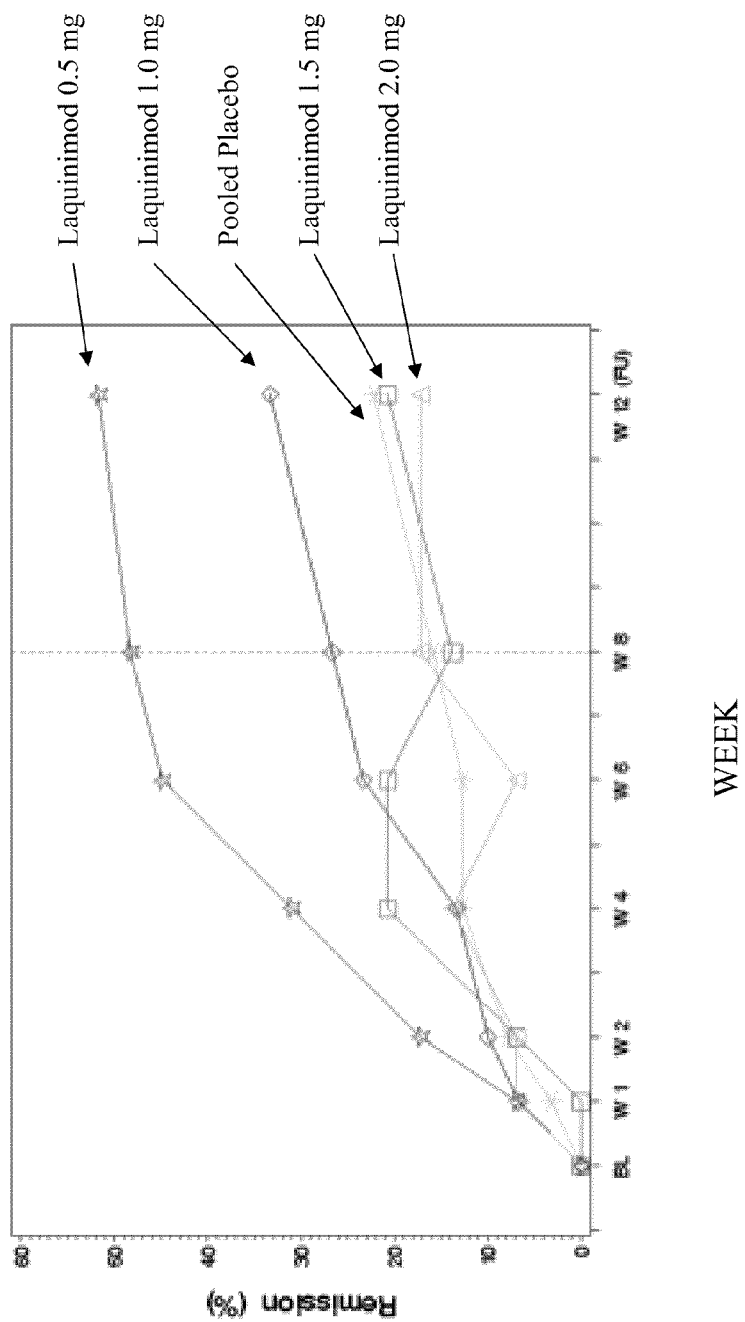
FIG. 2 shows the effect of laquinimod on Remission (by week) in Example 1.
Figure 3:
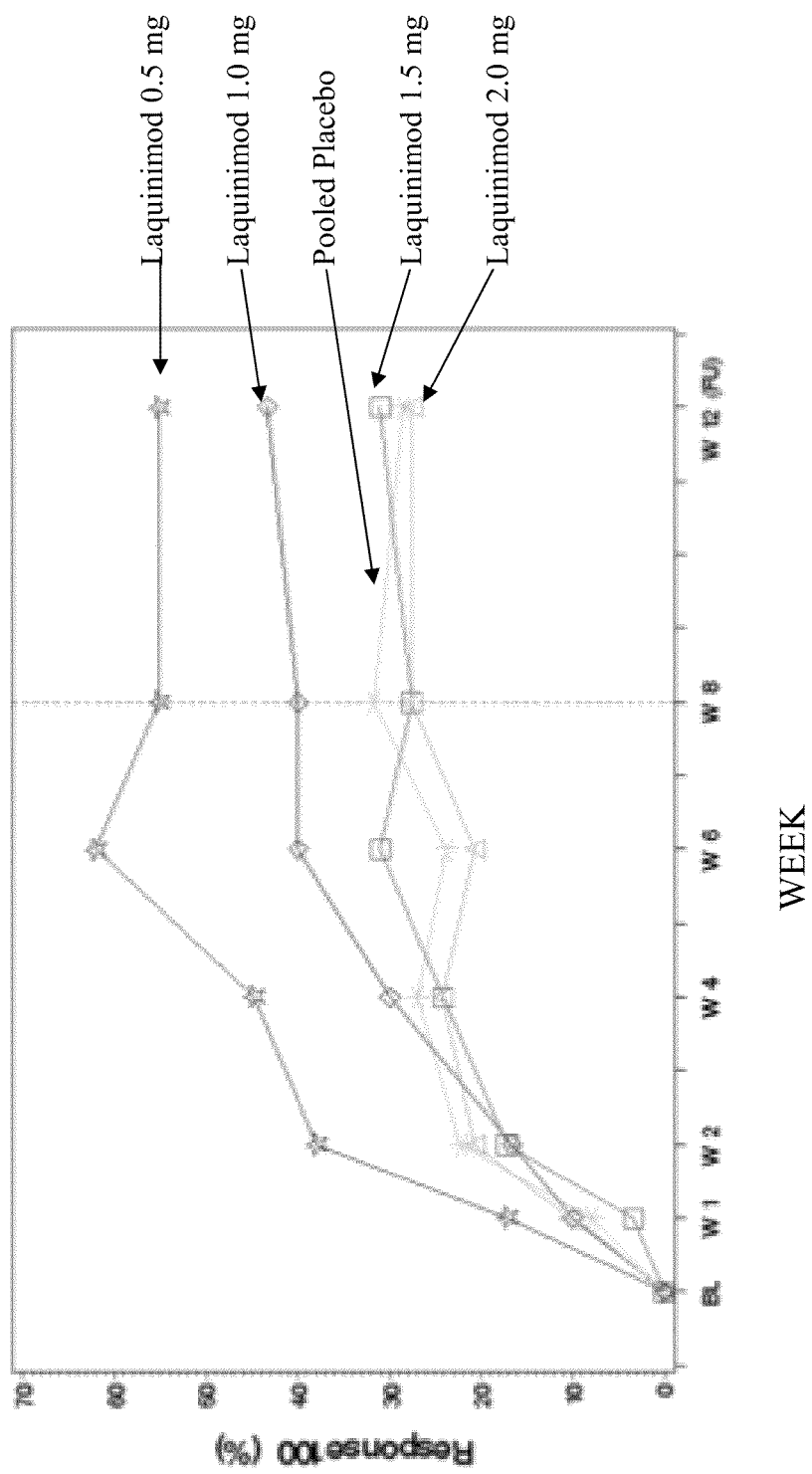
FIG. 3 shows the effect of laquinimod on Response 100 (by week) in Example 1.

At week 8, effects on remission and response 100 were observed with the 0.5 mg/day laquinimod dose. The 1 mg/day dose showed lower magnitude effects and higher laquinimod doses showed similar effects to placebo (see FIGS. 2 and 3).

Patients in the laquinimod 0.5 mg/day group achieved clinical remission (as early as week 2) and achieved response 100 (day 7) earlier than patients in the pooled placebo group.

Changes in Fecal Calprotectin Levels

All doses of laquinimod reduced fecal calprotectin with no evidence of any consistent dose related trends in the mean or median percent of change from baseline. Of those patients who had fecal calprotectin levels ≥250 μg/g at baseline, a greater percentage in the laquinimod groups (all doses) showed at least a 50% reduction and levels <250 μg/g at Week 8 compared to the pooled placebo group (26.7-38.9% vs. 13.6%, respectively).

TABLE 3

Changes in fecal calprotectin levels

| | Pooled Placebo | Laq 0.5 mg | Laq 1.0 mg | Laq 1.5 mg | Laq 2.0 mg |
|---|---|---|---|---|---|
| | % Change from Baseline in fecal calprotectin level at Week 8 | | | | |
| N | 50 | 24 | 27 | 25 | 21 |
| Mean ± SD | 91.0 ± 388.75 | 25.5 ± 132.93 | 0.2 ± 91.55 | 13.9 ± 108.97 | 44.3 ± 198.71 |
| Median | −16.0 | −23.1 | −14.4 | −18.7 | −20.1 |
| | % of patients with a calprotectin decrease from ≥250 μg/g to below 250 μg/g & greater than 50% reduction | | | | |
| N* | 44 | 18 | 18 | 15 | 11 |
| % Patients | 13.6% | 38.9% | 38.9% | 26.7% | 36.4% |

*Number of patients with calprotectin ≥250 μg/g at Baseline and non-missing calprotectin level at Week 8.

Safety Analysis

Adverse Events

The overall incidence of AEs ranged between 86.2-96.7% for the laquinimod groups versus 82.5% for the pooled placebo group. There was no apparent dose response relationship for the overall incidence of AEs. Most AEs were mild or moderate in severity.

Headache was the most common AE in all treatment groups, and the incidence of headache was higher in the laquinimod 2 mg/day group (44.8%) compared to other groups (Table 4).

The most common SAE was CD (exacerbation) reported by 3.4-6.9% of patients in the laquinimod groups versus 1.6% of patients in the pooled placebo group. Most other SAEs were reported by single patients. No subject died during the study.

There were no consistent trends in change from Baseline for any biochemical or hematological parameter in any of the dose groups or the pooled placebo group. Likewise, there were no clinically significant changes in vital signs or ECGs in the laquinimod dose groups.

TABLE 4

Common Adverse Events in Laquinimod Dose Groups Over Pooled Placebo

| Preferred Term (%) | Pooled Placebo (N = 63) | Laq 0.5 mg (N = 29) | Laq 1.0 mg (N = 30) | Laq 1.5 mg (N = 29) | Laq 2.0 mg (N = 29) |
|---|---|---|---|---|---|
| Headache | 20.6 | 24.1 | 26.7 | 24.1 | 44.8 |
| Abdominal Pain | 12.7 | 17.2 | 13.3 | 24.1 | 24.1 |
| Nausea | 6.3 | 3.4 | 20 | 6.9 | 20.7 |
| Vomiting | 7.9 | 17.2 | 20 | 3.4 | 20.7 |
| Abdominal Pain Upper | 4.8 | 3.4 | 0 | 6.9 | 17.2 |
| Myalgia | 1.6 | 0 | 3.3 | 0 | 17.2 |
| Pyrexia | 12.7 | 24.1 | 3.3 | 20.7 | 13.8 |
| Crohn's Disease$^a$ | 11.1 | 6.9 | 16.7 | 17.2 | 13.8 |
| Diarrhoea | 3.2 | 20.7 | 3.3 | 0 | 10.3 |
| Asthenia | 4.8 | 3.4 | 6.7 | 10.3 | 6.9 |
| Back Pain | 7.9 | 10.3 | 10 | 13.8 | 3.4 |
| Dizziness | 1.6 | 3.4 | 3.3 | 10.3 | 3.4 |
| Tachycardia | 0 | 0 | 0 | 10.3 | 3.4 |
| Cough | 3.2 | 6.9 | 10 | 6.9 | 3.4 |
| Abdominal Distension | 0 | 10.3 | 0 | 3.4 | 3.4 |
| Alanine Aminotransferase Increased | 1.6 | 0 | 10 | 0 | 3.4 |
| Rectal Haemorrhage | 0 | 0 | 3.3 | 10.3 | 0 |
| Fatigue | 3.2 | 6.9 | 0 | 10.3 | 0 |

Conclusions

This is the first study of laquinimod in active Crohns disease to be reported. The study indicates that treatment with laquinimod is well tolerated and that the 0.5 and 1 mg doses have clinically relevant effects on remission and response.

All doses (LAQ 0.5-2 mg/day) were found to reduce objective measures of intestinal inflammation in active CD.

Example 2

Assessment of Oral Laquinimod in Sub-Populations of Crohn's Disease Patients

A multicenter, randomized, double-blind, placebo-controlled, dose range finding study was conducted to evaluate escalating doses of Laquinimod in 4 distinct cohorts. This study was conducted according and with similar requirements as presented in Example 1.

Tables 5-8 summarize and present the different cohorts, number of subjects participating in each cohort and the percentage of remission according to the distinctive doses of laquinimod administered to the subject.

TABLE 5

Previous use of anti-TNFαs

| CD-LAQ-201 (Crohn's disease) | | Pooled Placebo (N = 63) | Laq 0.5 mg (N = 29) | Laq 1.0 mg (N = 30) | Laq 1.5 mg (N = 29) | Laq 2.0 mg (N = 29) |
|---|---|---|---|---|---|---|
| N | NO | 27 | 11 | 18 | 11 | 11 |
|  | YES | 36 | 18 | 12 | 18 | 18 |
| CDAI Change from Baseline - Mean ± SD | NO | −77.2 (±79.4) | −88.2 (±115.7) | −38.5 (±121.6) | −95.5 (±73.9) | −56.4 (±95.6) |
|  | YES | −55.1 (±112.5) | −102.7 (±168.0) | −36.8 (±90.0) | −18.4 (±76.2) | −102.2 (±118.5) |
| Remission - N (%) | NO | 7 (25.9%) | 6 (54.5%) | 2 18.2%) | 3 (27.3%) | 5 (27.8%) |
|  | YES | 3 (8.3%) | 8 (44.4%) | 3 (16.7%) | 1 (5.6%) | 3 (25.0%) |
| Responders100 - N (%) | NO | 12 (44.4%) | 6 (54.5%) | 3 (27.3%) | 5 (45.5%) | 6 (33.3%) |
|  | YES | 8 (22.2%) | 10 (55.6%) | 5 (27.8%) | 3 (16.7%) | 6 (50.0%) |
| Responders70 - N (%) | NO | 13 (48.1%) | 7 (63.6%) | 3 (27.3%) | 6 (54.5%) | 10 (55.6%) |
|  | YES | 9 (25.0%) | 11 (61.1%) | 5 (27.8%) | 3 (16.7%) | 6 (50.0%) |

TABLE 6

Oral steroids on Baseline

| CD-LAQ-201 (Crohn's disease) | | Pooled Placebo (N = 63) | Laq 0.5 mg (N = 29) | Laq 1.0 mg (N = 30) | Laq 1.5 mg (N = 29) | Laq 2.0 mg (N = 29) |
|---|---|---|---|---|---|---|
| N | NO | 46 | 19 | 18 | 20 | 24 |
|  | YES | 17 | 10 | 12 | 9 | 5 |
| CDAI Change from Baseline - Mean ± SD | NO | −55.4 (±102.7) | −85.3 (±164.3) | −59.4 (±112.6) | −46.8 (±78.1) | −39.7 (±100.6) |
|  | YES | −88.1 (±89.7) | −119.8 (±116.2) | −93.5 (±91.9) | −52.6 (±98.2) | −20.3 (±136.9) |

TABLE 6-continued

Oral steroids on Baseline

| CD-LAQ-201 (Crohn's disease) | | Pooled Placebo (N = 63) | Laq 0.5 mg (N = 29) | Laq 1.0 mg (N = 30) | Laq 1.5 mg (N = 29) | Laq2.0 mg (N = 29) |
|---|---|---|---|---|---|---|
| Remission - N (%) | NO | 6 (13.0%) | 8 (42.1%) | 4 (22.2%) | 2 (10.0%) | 4 (16.7%) |
|  | YES | 4 (23.5%) | 6 (60.0%) | 4 (33.3%) | 2 (22.2%) | 1 (20.0%) |
| Responders100 - N (%) | NO | 12 (26.1%) | 9 (47.4%) | 6 (33.3%) | 4 (20.0%) | 7 (29.2%) |
|  | YES | 8 (47.1%) | 7 (70.0%) | 6 (50.0%) | 4 (44.4%) | 1 (20.0%) |
| Responders70 - N (%) | NO | 13 (28.3%) | 11 (57.9%) | 9 (50.0%) | 5 (25.0%) | 7 (29.2%) |
|  | YES | 9 (52.9%) | 7 (70.0%) | 7 (58.3%) | 4 (44.4%) | 1 (20.0%) |

TABLE 7

Predominantly inflammatory vs. fibrostenotic

| CD-LAQ-201 (Crohn's disease) | | Pooled Placebo (N = 63) | Laq 0.5 mg (N = 29) | Laq 1.0 mg (N = 30) | Laq 1.5 mg (N = 29) | Laq2.0 mg (N = 29) |
|---|---|---|---|---|---|---|
| N | Inflammatory | 31 | 22 | 18 | 11 | 11 |
|  | Fibrostenotic | 32 | 7 | 12 | 18 | 18 |
| CDAI Change from Baseline - Mean ± SD | Inflammatory | −67.2 (±105.2) | −125.1 (±137.5) | −76.7 (±118.4) | −43.8 (±98.0) | −33.1 (±120.2) |
|  | Fibrostenotic | −61.8 (±95.2) | −9.3 (±156.5) | −65.8 (±79.0) | −51.8 (±75.3) | −40.7 (±91.2) |
| Remission - N (%) | Inflammatory | 6 (19.4%) | 13 (59.1%) | 6 (33.3%) | 2 (18.2%) | 2 (18.2%) |
|  | Fibrostenotic | 4 (12.5%) | 1 (14.3%) | 2 (16.7%) | 2 (11.1%) | 3 (16.7%) |
| Responders100 - N (%) | Inflammatory | 12 (38.7%) | 14 (63.6%) | 7 (38.9%) | 3 (27.3%) | 4 (36.4%) |
|  | Fibrostenotic | 8 (25.0%) | 2 (28.6%) | 5 (41.7%) | 5 (27.8%) | 4 (22.2%) |
| Responders70 - N (%) | Inflammatory | 13 (41.9%) | 15 (68.2%) | 11 (61.1%) | 4 (36.4%) | 4 (36.4%) |
|  | Fibrostenotic | 9 (28.1%) | 3 (42.9%) | 5 (41.7%) | 5 (27.8%) | 4 (22.2%) |

TABLE 8

Previous Operations

| CD-LAQ-201 (Crohn's disease) | | Pooled Placebo (N = 63) | Laq 0.5 mg (N = 29) | Laq 1.0 mg (N = 30) | Laq 1.5 mg (N = 29) | Laq2.0 mg (N = 29) |
|---|---|---|---|---|---|---|
| N | NO | 42 | 24 | 18 | 16 | 16 |
|  | YES | 21 | 5 | 12 | 13 | 13 |
| CDAI Change from Baseline - Mean ± SD | NO | −58.6 (±102.0) | −118.1 (±132.4) | −77.9 (±121.5) | −68.3 (±88.3) | −54.6 (±113.4) |
|  | YES | −76.7 (±96.0) | 3.2 (±194.2) | −66.0 (±81.3) | −26.0 (±73.9) | −14.2 (±84.2) |
| Remission - N (%) | NO | 8 (19.0%) | 13 (54.2%) | 6 (33.3%) | 4 (25.0%) | 3 (18.8%) |
|  | YES | 2 (9.5%) | 1 (20.0%) | 2 (16.7%) | 0 (0.0%) | 2 (15.4%) |
| Responders100 - N (%) | NO | 13 (31.0%) | 14 (58.3%) | 7 (38.9%) | 6 (37.5%) | 6 (37.5%) |
|  | YES | 7 (33.3%) | 2 (40.0%) | 5 (41.7%) | 2 (15.4%) | 2 (15.4%) |
| Responders70 - N (%) | NO | 14 (33.3%) | 15 (62.5%) | 10 (55.6%) | 7 (43.8%) | 6 (37.5%) |
|  | YES | 8 (38.1%) | 3 (60.0%) | 6 (50.0%) | 2 (15.4%) | 2 (15.4%) |

Results

Previous Treatment of Anti-TNFαs

This sub-cohort analysis describes remission rates at week 8 for patients who have previously received treatment with anti-TNFαs, any time in the past, versus those that did not. Patients, who have received anti-TNFαs in the past, tend to reflect a more severe, refractory segment of the Crohn's disease population. The results show that the effect seen for the 0.5 mg remains robust on both sub-populations. Patients who previously received anti-TNFαs that were treated with placebo tend to respond less than patients who did not receive anti-TNFαs in the past and were treated with placebo—this reflect the more severe disease of those who previously received anti-TNFαs (FIG. 1A).

Concomitant Treatment of Steroids and Laquinimod

This sub-cohort analysis describes remission rates at week 8 for patients who were on any dose of oral steroids (including budesonide) at study entry, versus those that did not. It illustrates the potential synergistic effect of oral steroids together with laquinimod, as approximately 60% of patients who were treated with oral steroids and received laquinimod 0.5 mg achieved remission vs. only about 40% on the complementary sub-cohort (no oral steroids)(FIG. 1B).

Inflammatory Vs. Fibrostenotic Crohn's Disease

Although CD usually is presented as acute or chronic bowel inflammation, the inflammatory process evolves toward one of two patterns of disease: a fibrostenotic-obstructing pattern or a penetrating-fistulous pattern, each with different treatments and prognoses.

This sub-cohort analysis describes remission rates at week 8 for patients who were classified as having a predominantly inflammatory disease (based on the Montreal classifications) versus those that have a fibrostenotic or penetrating disease. It suggests that laquinimod 0.5 mg and 1 mg may work better for patients with predominantly inflammatory disease vs the complementary cohort. While the effect of laquinimod 0.5 mg reached about 60% remission rate on the predominantly inflammatory sub-population, on the fibrostenotic or penetrating disease no effect for either the 0.5 mg or the 1 mg was noted (FIG. 1C).

Previous Crohn's Disease Operations

This sub-cohort analysis describes remission rates at week 8 for patients who had bowel resection any time in the past vs those that did not. Patients who did not have previous operations are patients on an earlier stage of their disease course or who has a predominantly inflammatory disease.

Although laquinimod 0.5 mg had an effect over placebo in both sub-populations, the magnitude of remitters on the segment with no previous operations was higher than 50% (FIG. 1D).

Example 3

Clinical Trial (Phase IIb)—Assessment of Oral Laquinimod in Active Moderate to Severe Crohn's Disease (LAQ-CD-202)

A phase IIb, multicenter, randomized, double-blind, placebo-controlled study is conducted to evaluate the efficacy, safety and tolerability of Laquinimod in active moderate to severe Crohn's disease.

Study Title

A Phase IIb, Multicenter, Randomized, Double-Blind, Placebo-Controlled Study to Evaluate the Efficacy, Safety, and Tolerability of Laquinimod in Active Moderate to Severe Crohn's Disease.

Number of Subjects 405 (approximately 135 per arm).

Method of Blinding and Randomization

During a Screening period of 1 to 2 weeks, the subjects are assigned a Screening number through the Interactive Voice/Web Response System (IVRS/IWRS). At the Baseline visit, subjects are assigned to 1 of the 3 possible treatment groups by the IVRS/IWRS in a 1:1:1 ratio.

The percentage of subjects treated with anti-TNF agents prior to Screening is limited to approximately 50%. Previous use of anti-TNF agents is used as a stratification factor.

Subjects who demonstrate a Response after 8 weeks of treatment (defined as reduction of CDAI by ≥70 points compared to baseline and total CDAI <220 at Week 8 with patient not designated a Treatment Failure (TF) during induction; in particular, this include patients in Remission) are eligible to be enrolled into a double-blind placebo controlled maintenance study (LAQ-CD-303, see Example 4), where they are re-randomized. Subjects who do not demonstrate a Response after 8 weeks of treatment are eligible to be enrolled into an open label induction and maintenance study (LAQ-CD-203).

Study Drug Dose, Mode of Administration, and Administration Rate

All subjects are administered laquinimod 0.25 mg, laquinimod 0.5 mg, and/or placebo capsules, taken orally at the same hour every day. Capsules should be swallowed with a glass of water.

Investigational Product:

Laquinimod 0.25 mg dose group—on each dosing occasion, 1×0.25 mg capsule and 1× placebo capsule for 0.5 mg are administered. On Days 1 and 2, this dose is administered twice daily (BID) as a loading dose (total daily dose 0.5 mg). Dosing is once daily (QD) from Day 3 onwards.

Laquinimod 0.5 mg dose group—on each dosing occasion, 1×0.5 mg capsule and 1× placebo capsule for 0.25 mg are administered. On Days 1 and 2, this dose is administered BID as a loading dose (total daily dose 1 mg). Dosing is QD from Day 3 onwards.

Laquinimod 0.25 mg and 0.5 mg capsules are packaged in high-density polyethylene, 50-mL (DUMA) bottles with 2 g of silica gel in cap, 35 capsules per bottle. Capsules should be swallowed with a glass of water at the same time each day.

Placebo:

Placebo capsules—on each dosing occasion, 1× placebo for 0.25 mg and 1× placebo for 0.5 mg capsules are administered; BID on Days 1 and 2 and QD from Day 3 onwards.

Matching placebo capsules are packaged in high-density polyethylene, 50-mL (DUMA) bottles with 2 g of silica gel in cap, 35 capsules per bottle. Capsules should be swallowed with a glass of water at the same time each day.

Study Duration

Each group is evaluated for up to 10 weeks: Screening, between 1-2 weeks; treatment period, 8 weeks. Subjects who do not subsequently enter either a maintenance or open-label induction study have a follow-up period of 4 weeks in the present study.

Study Population

Subjects with moderate to severe Crohn's disease (CD), as determined by a Crohn's Disease Activity Index (CDAI) score of 220-450 (inclusive).

Definitions

The following definitions are used in study:

Remission: subjects with CDAI <150 subjects not designated a Treatment Failure (TF).

Response 100: reduction of CDAI by at least 100 points compared to Baseline in subjects not designated a Treatment Failure (TF). Any subject with Remission is also considered to have achieved Response 100.

Response 70: reduction of CDAI by at least 70 points compared to Baseline, in subjects not designated a TF.

Treatment Failure: TF is defined as any new medication/treatment (including surgery) for CD or dose increase not allowed by the protocol, throughout the study period. Any early termination from the study is regarded as TF.

IBDQ Response: An increase from baseline in total IBDQ score of ≥16 points.

IBDQ Remission: A total IBDQ score of >170 points.

WPAI Minimally Important Difference (MID): A change in WPAI:CD score of 7%.

Minimal Clinically Important Difference (MCID): A change in the visual analog scale (VAS) component of the EQ-5D score of 4.2.

Calprotectin Response: the definition of fecal calprotectin response depends on the level at Baseline:

For Baseline fecal calprotectin level ≥250 µg/g, level needs to be reduced by at least 50% and be <250 µg/g.

For Baseline fecal calprotectin level ≥50 µg/g and <250 µg/g, level needs to be reduced by at least 50% compared to Baseline OR to <50 µg/g.

For Baseline fecal calprotectin level <50 µg/g, level needs to remain <50 µg/g.

Study Design and Methodology

This is a Phase IIb, randomized, double blind, placebo-controlled study to assess the efficacy, safety, and tolerability of 2 doses of laquinimod in active moderate to severe CD subjects. Treatment duration is 8 weeks. Scheduled in-clinic visits are conducted at Screening, Baseline (Week 0), and at Weeks 1, 2, 4, 6, and 8. Unscheduled visits for safety or for any other reason may be conducted at any time during the study This study evaluates the efficacy of a daily dose of 0.25 and 0.5 mg laquinimod compared to placebo with respect to the proportion of subjects in Remission (CDAI <150) at Week 8 with subjects not designated a treatment failure (TF), in subjects with active moderate to severe CD. This study also evaluates the safety and tolerability of a daily dose of 0.25 and 0.5 mg laquinimod compared to placebo in subjects with active moderate to severe CD.

In addition, this study evaluates the efficacy of a daily dose of 0.25 and 0.5 mg laquinimod compared to placebo with respect to Response 70 and Response 100, the efficacy of a daily dose of 0.25 and 0.5 mg laquinimod compared to placebo using the Inflammatory Bowel Disease Questionnaire (IBDQ).

This study also establishes the dose level(s) of laquinimod that is used in subsequent induction and maintenance studies in the same indication.

Further, this study evaluates the efficacy of a daily dose of 0.25 and 0.5 mg laquinimod compared to placebo with respect to fecal calprotectin response.

Finally, this study evaluates the efficacy of a daily dose of 0.25 and 0.5 mg laquinimod compared to placebo using the CD specific Work Productivity and Activity Impairment (WPAI) questionnaire and the EQ-5D questionnaire.

There are 3 treatment arms in the study: laquinimod 0.25 mg, laquinimod 0.5 mg, or placebo is administered daily (randomization ratio 1:1:1). A loading dose regimen of the study drug is given during the first 2 days of treatment (Day 1 [Baseline] and Day 2). The first loading dose of the study drug is administered at the site. The loading dose doubles the intended dose for the first 2 days and is administered BID with 12-hour intervals between dosing. Thereafter, starting on Day 3, the dosing regimen consists of the intended dose QD.

During the study period the CDAI score is assessed in addition to routine safety. Subjects are required to maintain CDAI diaries for each day of the Screening period and, if randomized, on each day of the treatment period. The scores obtained from the 7 consecutive diaries completed prior to the Baseline visit and to each of Weeks 1, 2, 4, 6, and 8 contribute to a total CDAI score at each of these time points.

Fecal calprotectin is assessed from stool samples collected at each visit up to Week 8/early termination. Serum CRP levels are assessed as part of the standard clinical laboratory evaluations. In addition, subjects are required to complete the IBDQ, CD-specific WPAI, and EQ-5D questionnaires at Baseline and Week 8.

In general, the dose of allowed concomitant medications is kept stable throughout the study. Any new medication/treatment for CD or dose increase not allowed by the protocol, throughout the study treatment period, results in a major protocol violation and is regarded as a Treatment Failure (TF). Decrease in dose or dose regimen not allowed by the protocol also results in a major protocol violation. CD surgery, biologic treatment, or new immunosuppressive drugs, throughout the study treatment period, are regarded as Treatment Failure (TF) and results in early treatment discontinuation.

The study includes an interim futility analysis after approximately 40 subjects in each of the 3 arms have completed 8 weeks of treatment. The futility analysis determines whether to continue as planned, drop a futile dose, or terminate the study. In the case that 1 dose is dropped, the study continues until reaching approximately 135 subjects in the placebo group and the laquinimod dose group being continued, and the randomization ratio changes to 1:1 (the total sample size is 135+135+40=310 subjects).

Inclusion/Exclusion Criteria
Inclusion Criteria
Subjects must meet all the inclusion criteria to be eligible:
1. Males and females 18-75 years old (inclusive).
2. Diagnosed CD for at least 3 months prior to Screening that has been appropriately documented and supported by endoscopy, radiology, or surgery (performed within 36 months prior to Screening).
3. Moderate to severe CD as determined by a CDAI score of 220-450 (inclusive).
4. Evidence of inflammatory disease, based on fecal calprotectin >250 µg/g and/or serum C-reactive protein (CRP) >5 mg/L at Screening or any time between Screening to Baseline, including at Baseline.
5. Subject is willing and able to provide written, informed consent.

Exclusion Criteria
Any of the following excludes the subject from entering the study:
1. A diagnosis of indeterminate or ulcerative colitis.
2. Positive results on stool culture for enteric pathogens (*Salmonella, Shigella, Yersinia, Campylobacter*, or *Clostridia difficile* toxin assay) at Screening.
3. Bowel surgery/resection within the 6 months prior to Screening and/or 2 or more resections where the indication was CD at any time during the life of the subject.
4. Clinically significant short bowel syndrome.
5. Clinically significant or symptomatic gastrointestinal obstructive symptoms.
6. Bowel perforation within 6 months prior to Screening.
7. Intra-abdominal abscess or suspected abscess.
8. Actively draining perianal or enterocutaneous fistulae, or other nonenterocutaneous fistulae.
9. Ostomy or ileoanal pouch.
10. Subjects who receive parenteral nutrition.
11. Oral corticosteroids treatment (eg, prednisolone/prednisone/budesonide) initiated less than 4 weeks prior to Screening.
12. Subjects treated with prednisone >15 mg/day (or equivalent) or budesonide >6 mg/day for CD at Baseline, or whose corticosteroid dosage regimen is not stable for at least 4 weeks prior to Baseline. (Stable dose defined as ≤2.5 mg prednisone [or equivalent] increase or decrease).
13. Intravenous (IV) or intramuscular (IM) corticosteroid administration within 8 weeks of Baseline.
14. Treatment with 5-aminosalicylic acid (5-ASA) that has not been at a stable dose for at least 2 weeks prior to Screening.
15. Antibiotics for CD at Screening that are not a stable dose for at least 2 weeks prior to Screening.
16. Treatment with 6-mercaptpurine (6-MP), azathioprine (AZA), or methotrexate (MTX) treatment that was initiated within 12 weeks prior to Screening or who are not on a stable dose for at least 6 weeks prior to Screening.
17. Subjects treated with anti-tumor necrosis factor (TNF) within 8 weeks prior to Screening.
18. Treatment with cyclosporine, tacrolimus, mycophenolate mofetil, or thalidomide within 2 months prior to Screening.
19. Natalizumab/vedolizumab/ustekinumab treatment within 6 months prior to Screening.
20. Subjects with a clinically significant or unstable medical or surgical condition that would preclude safe and complete study participation, as determined by medical history, physical examinations, electrocardiogram (ECG), or laboratory evaluations.

21. Subjects with planned or elective surgery or hospitalization during the course of the study that may interfere with study compliance or outcome.
22. Serum elevation ≥3×ULN of alanine aminotransferase (ALT) or aspartate aminotransferase (AST) at Screening.
23. Serum elevation ≥2×ULN of direct bilirubin at Screening.
24. A QTc interval >500 msec (according to machine output), obtained from 2 ECG recordings at Screening visit OR the mean value calculated from 2 Baseline ECG recordings.
25. Any history of malignancy in the last year, prior to Screening, excluding basal cell carcinoma.
26. Use of any other investigational drugs within 3 months prior to Screening.
27. Use of moderate and strong inhibitors of cytochrome P450 (CYP) 3A4 within 2 weeks prior to Baseline visit (1 month for fluoxetine).
28. Amiodarone within 2 years prior to Screening visit.
29. Women who are pregnant or nursing at the time of Screening, or who intend to be during the study period.
30. Women of child-bearing potential who do not practice an acceptable method of birth control. (Acceptable methods of birth control in this study are: surgical sterilization, intrauterine devices, oral contraceptive, contraceptive patch, long-acting injectable contraceptive, partner's vasectomy, a double-protection method [condom or diaphragm with spermicide]).
31. Known drug hypersensitivity that would preclude administration of the study drug, such as hypersensitivity to: mannitol, meglumine, or sodium stearyl fumarate.
32. Subjects unable to comply with the planned schedule of study visits and study procedures.

Outcome Measures

Primary Efficacy Endpoint:

The primary efficacy endpoint is the proportion of subjects achieving Remission (CDAI <150) at Week 8 with subjects not designated a Treatment Failure (TF).

Secondary Efficacy Endpoints:

Proportion of subjects achieving Response 70 at Week 8.
Proportion of subjects achieving Response 100 at Week 8.
Mean change in total IBDQ score from Baseline to Week 8.
Proportion of subjects with an IBDQ Response at Week 8.
Proportion of subjects with IBDQ Remission at Week 8.

Other Efficacy Endpoints:

Proportion of subjects achieving Remission, Response 70, and Response 100 at each visit prior to Week 8.
CDAI mean change from Baseline at each visit.
Time to Remission.
Time to Response 70.
Time to Response 100.
Proportion of subjects achieving fecal calprotectin response by visit.
Proportion of subjects achieving fecal calprotectin response and Remission by visit
Proportion of subjects achieving fecal calprotectin response and Response 70 by visit
Proportion of subjects achieving fecal calprotectin response and Response 100 by visit
Fecal calprotectin mean percentage change from Baseline by visit.
Mean changes in scores from Baseline to Week 8, for each of the four IBDQ domain scores
Changes in each of the scores of the CD-specific WPAI (WPAI:CD) questionnaire from Baseline to Week 8.
Proportion of subjects achieving at least MID (7%) in WPAI:CD score at Week 8.
EQ-5D questionnaire results at Week 8.
Proportion of subjects achieving at least MCID (4.2) in the VAS component of the EQ-5D questionnaire at Week 8.

Safety Variables and Endpoints: Safety variables and endpoints include Adverse events (AEs), Clinical laboratory values, Vital signs, and ECG.

Tolerability Variables and Endpoints: Tolerability endpoints include the proportion of subjects who prematurely discontinue treatment, the proportion of subjects who prematurely discontinue treatment due to AEs, the time to premature treatment discontinuation, and the time to premature treatment discontinuation due to AEs.

Results

The 0.25 mg/day laquinimod are effective to induce Remission (CDAI <150) in the subjects by Week 8.
The 0.25 mg/day laquinimod are effective to induce Response 70 and/or Response 100 in the subjects by Week 8.
The 0.25 mg/day laquinimod are effective to improve the subjects' IBDQ score from Baseline by Week 8.
The 0.25 mg/day laquinimod are effective to induce IBDQ Response and/or IBDQ Remission by Week 8.
The 0.5 mg/day laquinimod are effective to induce Remission (CDAI <150) in the subjects by Week 8.
The 0.5 mg/day laquinimod are effective to induce Response 70 and/or Response 100 in the subjects by Week 8.
The 0.5 mg/day laquinimod are effective to improve the subjects' IBDQ score from Baseline by Week 8.
The 0.5 mg/day laquinimod are effective to induce IBDQ Response and/or IBDQ Remission by Week 8.

Example 4

Clinical Trial (Phase III)—52-Week Maintenance of Remission Study in Active Moderate to Severe Crohn's Disease (LAQ-CD-303)

A phase III, randomized, double-blind, placebo-controlled 52-week maintenance of remission study is conducted in active moderate to severe Crohn's disease patients.

Study Title

A Phase III, Randomized, Double-Blind, Placebo-Controlled 52-week Maintenance of Remission Study in Moderate to Severe Crohn's Disease Patients.

Number of Subjects 160 subjects per arm (320 or 480 subjects, depending on whether 2 or 3 arms are included) are included in the primary efficacy cohort (PEC) of this study. The PEC consists only of subjects who are Responders to an effective laquinimod dose in of 3 induction studies (LAQ-CD-202, LAQ-CD-301, and LAQ-CD-302); the total number of subjects enrolled in the study is greater than the sum of Responders from the 3 induction studies, as some of the subjects are Responders to placebo or an ineffective laquinimod dose in the induction studies. The effective dose is based on the overall benefit/risk results of study LAQ-CD-202.

Method of Blinding and Randomization

Study LAQ-CD-202 evaluates 0.25 and 0.5 mg daily doses of laquinimod compared to placebo, and based on its results, the dose(s) for LAQ-CD-303 are chosen. LAQ-CD-303 starts to enroll subjects before dose selection is done, so at the start of LAQ-CD-303 subjects are randomized at a 1:1:1 ratio to 0.25 mg, 0.5 mg or placebo. After dose selection, the randomization ratio remains 1:1:1 or change to 1:1 if only 1 dose of laquinimod is continued.

Subjects are stratified by Remission status at entrance (CDAI <150; CDAI 150), induction study they attended (LAQ-CD-202; LAQ-CD-301; LAQ-CD-302), dose received in the induction study, and by previous use of anti-TNF agents.

At the Baseline visit, subjects are assigned to 1 of the possible treatment groups by the Interactive Voice/Web Response System (IVRS/IWRS).

Subjects who demonstrate a Response after 8 weeks of treatment in 1 of the induction studies are eligible to be enrolled into LAQ-CD-303 and are re-randomized.

Study Drug Dose, Mode of Administration, and Administration Rate

Investigational Product:

Laquinimod 0.25 mg dose group—1×0.25 mg laquinimod capsule and 1× placebo for 0.5 mg capsule once daily (QD).

Laquinimod 0.5 mg dose group—1×0.5 mg laquinimod capsule and 1× placebo for 0.25 mg capsule QD.

Laquinimod capsules for both doses are packaged in round 50-mL white high density polyethylene bottles. Capsules should be swallowed with a glass of water at the same time each day.

Placebo:

Matching placebo capsules—2 placebo capsules QD (1× placebo for 0.25 mg and 1× placebo for 0.5 mg.

Matching placebo capsules are packaged in round 50-mL white high density polyethylene bottles. Capsules should be swallowed with a glass of water.

Study Duration

Each group is evaluated for 52 weeks. Subjects who do not subsequently enter the open-label extension study (Study LAQ-CD-303E) have a follow-up period of 4 weeks in the present study.

Study Population

Subjects with a Response during the 8-week induction studies LAQ-CD-202, LAQ-CD-301, or LAQ-CD-302 are re-randomized into this placebo-controlled maintenance study. Response in those induction studies was defined as a Crohn's Disease Activity Index (CDAI) reduction of at least 70 points from Baseline and CDAI <220 at Week 8 of the induction study in the absence of treatment failure (TF); in particular, this included subjects in Remission. In those 3 induction studies, TF was defined as follows: any new medication/treatment (including surgery) for Crohn's disease (CD) or dose increase not allowed by the protocol, throughout the study period; any early termination from the study was also regarded as TF. No de novo subjects are included in this study.

Definitions

The following definitions are used in study:

Primary Efficacy Cohort (PEC): The PEC consists of subjects who were Responders to an effective laquinimod dose in 1 of 3 induction studies (LAQ-CD-202, LAQ-CD-301, and LAQ-CD-302) and are randomized to receive placebo or the chosen dose(s) during maintenance. In the case that only 1 dose is chosen for the maintenance study, then only 2 arms are compared for efficacy: placebo and the chosen dose.

Remission: Subjects with CDAI <150 with no Treatment Failure (TF) during the course of the study.

Treatment Failure (TF): TF is defined in this study as 1) subject failing to taper down their corticosteroids as required by the protocol; 2) subject receiving new CD medications or increasing the dose of concomitant medications not allowed by the protocol; 3) surgery for CD; and 4) any early termination prior to completing 52 weeks of treatment.

Steroid Free: Subjects are considered steroid free after the following taper-down scheme: prednisolone—in decrements not greater than 5 mg/2 weeks for tapering down to 10 mg/day, and in decrements not greater than 2.5 mg/2 weeks for tapering down to lower than 10 mg/day. Budesonide taper—3 mg/4 weeks. From Week 12 and until the end of the study—steroid dose should remain stable.

Steroid Free Remission: Subjects achieving both Remission and steroid free.

IBDQ Response: An increase from baseline in total IBDQ score of ≥16 points.

IBDQ Remission: A total IBDQ score of >170 points.

WPAI Minimally Important Difference (MID): A change in WPAI:CD score of 7%.

Calprotectin Response: The definition of fecal calprotectin response depends on the level at Baseline:

For Baseline fecal calprotectin level ≥250 μg/g, level needs to be reduced by at least 50% and to be <250 μg/g.

For Baseline fecal calprotectin level ≥50 μg/g and <250 μg/g, level needs to be reduced by at least 50% compared to Baseline OR to <50 μg/g.

For Baseline fecal calprotectin level <50 μg/g, level needs to remain <50 μg/g.

Study Design and Methodology

This is a Phase III, randomized, double blind, placebo controlled 52-week maintenance of Remission study in subjects with moderate to severe CD who had a Response in a previous induction study.

This study evaluates, for subjects in the PEC, the efficacy of laquinimod with respect to Remission (CDAI <150) in subjects with CD at Week 52 and the efficacy of laquinimod with respect to sustaining clinical Remission in subjects with CD (defined as Remission at Week 36 and Week 52).

This study also evaluates, the efficacy of laquinimod with respect to maintaining steroid-free Remission at Week 52, the efficacy of laquinimod using the Inflammatory Bowel Disease Questionnaire (IBDQ) at Week 52, and the long-term (52 weeks) safety and tolerability of laquinimod in CD subjects.

In addition, this study evaluates, for subjects in the PEC, the efficacy of laquinimod with respect to sustaining Remission (defined as Remission at Week 36 and Week 52) only in subjects who were in Remission at study entrance; the efficacy of laquinimod with respect to Remission at Week 12 in subjects who were Responders but were not in Remission at study entrance; the efficacy of laquinimod with respect to sustaining Remission (defined as Remission at Week 36 and Week 52) in subjects who were Responders but were not in Remission at study entrance; the efficacy of laquinimod using the CD-specific Work Productivity and Activity Impairment (WPAI:CD) Questionnaire and the EQ-5D questionnaire; and To the efficacy of laquinimod with respect to fecal calprotectin response.

The study starts with 3 treatment arms in the study: laquinimod 0.25 mg, laquinimod 0.5 mg, and matching placebo (randomization ratio 1:1:1). After dose selection from the LAQ-CD-202 induction study, subjects with a Response from LAQ-CD-202 (after the time of the futility analysis in the case of 1 dose being dropped), LAQ-CD-301, or LAQ-CD-302 induction studies are randomized to receive the selected effective laquinimod dose(s) (0.25 and/or 0.5 mg) or placebo in equal proportions (i.e., 1:1 ratio if only 1 dose of laquinimod is chosen and 1:1:1 ratio if 2 doses of laquinimod are chosen).

Treatment duration is 52 weeks. Scheduled in-clinic visits are conducted at Baseline (Week 0), and at Weeks 2, 4, 8, 12, 16, 20, 28, 36, 44, and 52. The Week 0 visit for this maintenance study is the same as the Week 8 visit in the induction study. Unscheduled visits for safety or for any other reason may be conducted at any time during the study. Subjects completing the study have the option to enroll into its open-label extension (Study LAQ-CD-303E), where they may receive the chosen maintenance dose of laquinimod up to marketing authorization/availability of the product in the market. Subjects who do not enter Study LAQ-CD-303E have a follow-up period of 4 weeks in the present study.

All subjects on oral steroids (up to 15 mg prednisolone or 6 mg budesonide) at study entry are required to taper down their steroid dose until steroid free on Week 12. [Prednisolone—in decrements not greater than 5 mg/2 weeks for tapering down to 10 mg/day, and in decrements not greater than 2.5 mg/2 weeks for tapering down to lower than 10 mg/day; budesonide, 3 mg/4 weeks]. From Week 12 and until the end of the study (52 weeks)—steroid dose should remain stable.

In general, the dose of allowed concomitant medications are kept stable throughout the study. Any new medication/treatment for CD or dose increase not allowed by the protocol, throughout the study treatment period, results in a major protocol violation and is regarded as a Treatment Failure (TF). CD surgery or a failure to taper down corticosteroids as required by the protocol are regarded as TF and result in early treatment discontinuation.

During the study period CDAI score is assessed in addition to routine safety. Subjects are required to maintain CDAI diaries on a daily basis for the 7 days prior to each visit of the treatment period; subjects receive a reminder prompt (e.g., by e-mail, text message, etc.) prior to the start of each 7-day collection period. The scores obtained from the 7-day diaries completed prior to the Baseline visit (taken from the diaries from their final week in the previous induction study) and to each of the post-Baseline visits (starting at Week 2) contribute to a total CDAI score at each of these time points.

In addition, subjects are required to complete the IBDQ, CD-specific WPAI (WPAI:CD), and EQ-5D questionnaires at Baseline, Week 28 and Week 52. The IBDQ is a disease-specific, 32-item health-related quality of life questionnaire that assesses 4 dimensions: (1) bowel symptoms, (2) systemic symptoms, (3) social function, and (4) emotional function. The WPAI:CD is a validated, 6-question instrument that assesses the impact of CD on work and activity during the past 7 days. The EQ-5D is a 6-item, self-administered questionnaire designed to measure health status.

Fecal calprotectin is assessed from stool samples collected at each visit. Serum CRP levels are assessed as part of the standard clinical laboratory evaluations.

Inclusion/Exclusion Criteria

Inclusion Criteria

Subjects must meet all the inclusion criteria to be eligible:
1. Subject met all of the inclusion criteria from the previous induction study (LAQ-CD-202, LAQ-CD-301 or LAQ-CD-302).
2. Subject has a clinical Response (defined as a CDAI reduction of at least 70 points from Baseline and CDAI <220 at Week 8 of the induction study in the absence of TF; this included subjects in Remission) from previous induction studies (LAQ-CD-202, LAQ-CD-301, or LAQ-CD-302).
3. Subjects willing and able to provide written, informed consent.

Exclusion Criteria

Any of the following excludes the subject from entering the study:
1. Subject Met one or more of the exclusion criteria from the previous induction study (LAQ-CD-202, LAQ-CD-301, or LAQ-CD-302).
2. Subjects unable to comply with the planned schedule of study visits and study procedures.

Outcome Measures

Primary Efficacy Endpoint:
The primary endpoint is evaluated for subjects who belong to the PEC.
The proportion of subjects in Remission at Week 52.

Secondary Efficacy Endpoints:
The secondary endpoints are evaluated for subjects who belong to the PEC.
The proportion of subjects in Sustained Remission (defined as Remission at Week 36 and Week 52).
The proportion of subjects with Steroid-free Remission at Week 52.
Mean change in total IBDQ score from Baseline to Week 52.
Proportion of subjects with an IBDQ Response at Week 52.
Proportion of subjects with IBDQ Remission at Week 52.

Other Efficacy Endpoints:
The other efficacy endpoints are evaluated for subjects who belong to the PEC.
Proportion of subjects in sustained Remission who were in Remission at study entrance.
Proportion of subjects who achieved Remission after 12 weeks in LAQ-CD-303 who were Responders but were not in Remission at study entrance.
Proportion of subjects in sustained Remission who were Responders but were not in Remission at study entrance.
Proportion of subjects in Remission at each visit prior to Week 52.
CDAI mean change from Baseline by visit.
Proportion of subjects with an increase in CDAI.
Mean change in scores from Baseline to Week 52 for each of the 4 IBDQ domain scores.
Mean change in total IBDQ score and by domain from Baseline to Week 28.
Change in each of the scores from the CD-specific WPAI (WPAI:CD) questionnaire from Baseline to Week 28 and Week 52.
Proportion of subjects achieving at least MID (7%) in WPAI:CD score at Week 28 and Week 52.
EQ-5D questionnaire results at Week 28 and Week 52.
Proportion of subjects achieving at least MCID (4.2) in the VAS component of the EQ-5D questionnaire at Week 28 and Week 52.
Proportion of subjects achieving fecal calprotectin response by visit.
Proportion of subjects achieving fecal calprotectin response and in Remission by visit.
Fecal calprotectin mean percent change from Baseline by visit.

Safety Variables and Endpoints: Safety variables and endpoints include Adverse events (AEs), Clinical laboratory values, Vital signs, and ECG.

Tolerability Variables and Endpoints:
Tolerability variables and endpoints are presented for all subjects who entered the study and separately for subjects included in the PEC, and include the proportion of subjects who prematurely discontinue treatment, the proportion of subjects who prematurely discontinue treatment due to AEs, the time to premature treatment discontinuation, and the time to premature treatment discontinuation due to AEs.

Pharmacokinetics, pharmacodynamics and Pharmacogenetics are not assessed in this study.

Results

The 0.25 mg/day laquinimod are effective to induce and/or maintain Remission in subjects by Week 52.

The 0.25 mg/day laquinimod are effective to sustain Remission in subjects (Remission at Week 36 and Week 52).

The 0.25 mg/day laquinimod are effective to induce and/or maintain steroid-free Remission in subjects by Week 52.

The 0.25 mg/day laquinimod are effective to improve and/or maintain IBDQ score in subjects by Week 52.

The 0.25 mg/day laquinimod are effective to induce and/or maintain IBDQ Response in subjects by Week 52.

The 0.25 mg/day laquinimod are effective to induce and/or maintain IBDQ Remission in subjects by Week 52.

The 0.5 mg/day laquinimod are effective to induce and/or maintain Remission in subjects by Week 52.

The 0.5 mg/day laquinimod are effective to sustain Remission in subjects (Remission at Week 36 and Week 52).

The 0.5 mg/day laquinimod are effective to induce and/or maintain steroid-free Remission in subjects by Week 52.

The 0.5 mg/day laquinimod are effective to improve and/or maintain IBDQ score in subjects by Week 52.

The 0.5 mg/day laquinimod are effective to induce and/or maintain IBDQ Response in subjects by Week 52.

The 0.5 mg/day laquinimod are effective to induce and/or maintain IBDQ Remission in subjects by Week 52.

References

1. PCT International Application Publication No. WO 2007/047863, published Apr. 26, 2007, international filing date Oct. 18, 2006.
2. PCT International Application Publication No. WO 2007/146248, published Dec. 21, 2007, international filing date Jun. 12, 2007.
3. Best et al. (1976) Development of a Crohn's Disease Activity Index. Gastroenterology; 70:439-444.
4. Best et al. (1979) Rederived values of the eight coefficients of the Crohn's Disease Activity Index (CDAI). Gastroenterology; 77:843-6.
5. Chamouard et al. Diagnostic value of C-reactive protein for predicting activity. Clin Gastroenterol hepatol; 4:882-887.
6. Colombel et al. (2004) The safety profile of infliximab in patients with Crohn's disease: the Mayo clinic experience in 500 patients. Gastroenterol; 126:19-31.
7. Colombel et al. (2007) Adlimumab for maintenance of clinical response and remission in patients with Crohn's disease: the CHARM trial. Gastroenterol; 132(1):52-65.
8. Comi et al. (2012) Placebo-controlled trial of oral laquinimod for multiple sclerosis. N Engl J Med; 366(11):1000-1009.
9. Comi et al. (2008), for the LAQ/5062 Study Group. Effect of laquinimod on MRI-monitored disease activity in patients with relapsing-remitting multiple sclerosis: a multicentre, radomised, double-blind, placebo-controlled phase IIB study. Lancet; 371:2085-92.
10. Denis et al. (2007) Assessment of Endoscopic Activity Index and Biological Inflammatory Markers in Clinically Active Crohn's disease with Normal C-reactive Protein Serum Level. Inflamm Bowel Dis; 13:1100-1105.
11. Dignass et al. (2010) "The second European evidence-based consensus on the diagnosis and management of Crohn's disease: Current management" Journal of Crohn's and Colitis 4:28-62.
12. EMEA 2007. Points to consider on clinical investigation of medicinal products for the management of Crohn's disease. CPMP/EWP/2284/99 Rev.1.
13. Everett and Hamlin (2011) "Evidence-based Use of Anti-INFα Therapy in Crohn's Disease" Frontline Gastroenterol. 2(3):144-150.
14. Friedman et al., eds. Harrison's Principles of Internal Medicine. New York: McGraw-Hill Professional, 2001: 1679-92.
15. Froehlich F (2007) "Fibrostenotic Crohn's disease" Digestion. 76(2):113-5. Epub 2008 Feb. 7.
16. Ghosh et al. (2003) Natalizumab for active Crohn's disease. N. Engl J Med; 348:24-32.
17. Guindi M and Riddell, RH (2004) "Indeterminate Colitis" J. Clin. Pathol. 57:1233-1244.
18. Hanauer et al. (2002) Maintenance infliximab for Crohn's disease: the accent I randomised trial. Lancet; 359.
19. Hendrickson et al. (2002) Clinical aspects and pathophysiology of inflammatory bowel disease. Clin Microbiol Rev; 15:79-94.
20. Hommes and Van Deventer (2003) Inflixmab therapy in Crohn's disease: safety issues. Neth J Med; 61:100-104.
21. Jonsson et al. (2004 Apr. 8) Synthesis and biological evaluation of new 1,2-dihydro-4-hydroxy-2-oxo-3-quinolinecarboxamides for treatment of autoimmune disorders: structure-activity relationship. J Med Chem. 47(8):2075-88.
22. Kasper et al. (2008) *Harrison's principles of internal medicine* (17th ed.). New York: McGraw-Hill Medical Publishing Division. ISBN 978-0-07-146633-9.
23. Kozuch and Hanauer (2008) Treatment of inflammatory bowel disease: A review of medical therapy. World J Gastroenterol; 14(3):354-377.
24. Laquinimod Investigator's Brochure (IB), Ed. 4, November 2007. Addendum No. 1. June, 2008, Supplement to Investigator's Brochure, Ed. 4, November, 2007.
25. Loftus et al. (2002) The epidemiology and natural history of Crohn's disease in population-based patient cohorts from North America: a systematic review. Aliment Pharmacol Ther; 16(1):51-60.
26. Lund Research Center AB, Active Biotech Group, Sweden. The inhibitory activity of PNU-215062 on acute experimental autoimmune encephalomyelitis in the mouse and a comparison with the activity of roquinimex (PNU-212616). 9830161, Final Report February 1999.
27. Mannon (2007) "GAIN for Loss: Adalimumab for Infliximab-Regractory Crohn Disease" Ann. Intern. Med. 146 (12):888-890.
28. Peyrin-Biroulet et al. (2010) The natural history of adult Crohn's disease in population-based cohorts. Am J Gastroenterol; 105(2):289-297.
29. Rieder et al. (2011) "Predictors of Fibrostenotic Crohn's Disease" Inflamm Bowel Dis. 17(9):2000-2007.
30. Sandborn et al. (2005) Natalizumab induction and maintenance therapy for Crohn's disease. N Engl J. Med. 353 (18):1912-25.
31. Sandborn et al. (2002) A review of activity indices and efficacy endpoints for clinical trials of medical therapy in adults with Crohn's disease. Gastroenterology. 512-530.
32. Schreiber et al. (2007) Maintenance therapy with centrolizumab pegol for Crohn's disease. N Engl J Med. 357:239-50.
33. Schreiber et al. (2005) A randomized, placebo-controlled trial of certolizumab pegol (CDP870) for treatment of Crohn's disease. Gastroenterol; 129:807-818.
34. Silverberg et al. (2005) Toward an integrated clinical, molecular and serological classification of inflammatory bowel disease: Report of a Working Party of the 2005 Montreal World Congress of Gastroenterology. Can J Gastroenterol. 2005; 19 Suppl A:5-36.

35. Solem et al. (2005) Correlation of C-reactive protein with clinical, endoscopic, histologic, and radiographic activity in Inflammatory Bowel disease. Inflamm Bowel Dis. 11(8):707-12.
36. Sweetman et al., editors. Martindale: The complete drug reference. London: Pharmaceutical Press. Electronic version, (Edition 35 [2006]).
37. Targan et al. (2007) Natalizumab for the treatment of active Crohn's disease: result of the ENCORE Trial. Gastrolenterology. 132(5):1672-83.
38. Targan et al. (1977) A short-term study of chimeric monoclonal antibody cA2 to tumor necroseis factor alpha for Crohn's disease. N. Engl J Med; 337:1029-35.
39. Thomas et al. (2004) Demyelination during anti-tumor necrosis factor alpha therapy with infliximab for Crohn's disease. Inflamm Bowel Dis; 10:28-31.
40. Van Assche et al. (2005) Progressive multifocal leukoencephalopathy after natalizumab therapy for Crohn's disease. N Engl J Med 2005; 353:362-8.
41. Vermeire et al. (2003) Autoimmunity associated with anti-tumor necrosis factor alpha treatment in Crohn's disease: a prospective cohort study. Gastroenterol; 125:32-9.
42. Wen and Fiocchi (2004) Inflammatory bowel disease: autoimmune or immune-mediated pathogenesis? Clin Develop Immunol; 11:195-204.
43. Wu, George. Crohn Disease, Emedicine, 2007.

What is claimed is:

1. A method of treating a human patient afflicted with anti-TNFα refractory Crohn's disease, the method comprising periodically administering to the patient an amount of laquinimod or pharmaceutically acceptable salt thereof effective to treat the patient.

2. The method of claim 1, wherein the Crohn's disease is non-fibrostenotic Crohn's disease.

3. The method of claim 2, wherein the Crohn's disease is inflammatory Crohn's disease.

4. The method of claim 1, wherein the Cretin's disease is steroid refractory Crohn's disease.

5. The method of claim 1, wherein the patient has been administered oral steroids at baseline.

6. The method of claim 1, wherein the patient's Crohn's disease had not been surgically treated.

7. The method of claim 1, wherein the Crohn's disease is refractory to anti-TNFα treatment using infliximab, adalimimab, certolizumab or natalizumab.

8. The method of claim 1, wherein the patient is naïve to anti-TNFα treatment.

9. The method of claim 1, wherein the amount of laquinimod is effective to reduce a symptom of Crohn's disease in the subject, induce clinical response, induce or maintain clinical remission, inhibit disease progression, or inhibit a disease complication in the subject.

10. The method of claim 9, wherein the amount of liaquinimod is effective to induce clinical remission in the patient.

11. The method of claim 9, wherein the amount of liaquinimod is effective to maintain clinical remission in the patient.

12. The method of claim 9, wherein the amount of laquinimod is effective to induce and maintain clinical remission in the patient.

13. The method of claim 1, wherein the amount is administered by a unit dose of 0.25 mg of laquinimod or a unit dose of 0.5 mg of laquinimod.

14. The method of claim 1, wherein the amount of laquinimod is 0.1-1.0 mg/day.

15. The method of claim 14, wherein the amount of laquinimod is 0.25 mg/day, 0.5 mg/day or 1.0 mg/day.

16. The method of claim 1, wherein the pharmaceutically acceptable salt of laquinimod is laquinimod sodium.

17. The method of claims 1, wherein the periodic administration is oral.

18. The method or claims 1, wherein the periodic administration is daily administration.

19. The method of claim 14 wherein the amount of laquinimod is 0.1-0.75 mg/day.

20. The method of claim 14, wherein the amount of laquinimod is 0.3-0.7 mg/day.

21. The method of claim. 1, wherein the laquinimod is administered as adjunct therapy with an other Crohn's disease treatment.

* * * * *